US012661196B2

(12) United States Patent
Cameron et al.

(10) Patent No.: US 12,661,196 B2
(45) Date of Patent: Jun. 23, 2026

(54) SYSTEM FOR NEURONAVIGATION REGISTRATION AND ROBOTIC TRAJECTORY GUIDANCE, ROBOTIC SURGERY, AND RELATED METHODS AND DEVICES

(71) Applicant: GLOBUS MEDICAL, INC., Audubon, PA (US)

(72) Inventors: Hayden Cameron, Philadelphia, PA (US); Spiros Mantzavinos, Nashua, NH (US); Neil R. Crawford, Chandler, AZ (US); Sanjay Joshi, Andover, MA (US); Norbert Johnson, North Andover, MA (US); James Cascarano, Cambridge, MA (US); Justin Larson, Reading, MA (US)

(73) Assignee: Globus Medical, Inc., Audubon, PA (US)

( * ) Notice: Subject to any disclaimer, the term of this patent is extended or adjusted under 35 U.S.C. 154(b) by 92 days.

(21) Appl. No.: 18/898,897

(22) Filed: Sep. 27, 2024

(65) Prior Publication Data

US 2025/0017669 A1     Jan. 16, 2025

Related U.S. Application Data

(60) Division of application No. 18/150,527, filed on Jan. 5, 2023, now Pat. No. 12,127,803, which is a division
(Continued)

(51) Int. Cl.
    *A61B 34/30*       (2016.01)
    *A61B 34/10*       (2016.01)
    (Continued)

(52) U.S. Cl.
    CPC .............. *A61B 34/30* (2016.02); *A61B 90/14* (2016.02); *A61B 2034/107* (2016.02); *A61B 2090/103* (2016.02); *A61B 2090/3983* (2016.02)

(58) Field of Classification Search
    CPC ...... A61B 2034/107; A61B 2034/2055; A61B 2090/103; A61B 2090/309;
         (Continued)

(56) References Cited

U.S. PATENT DOCUMENTS 4,150,293 A     4/1979   Franke
4,592,352 A     6/1986   Patil
          (Continued)

FOREIGN PATENT DOCUMENTS

DE     202008009571 U1    10/2008
DE     102014226240 A1     6/2016
          (Continued)

OTHER PUBLICATIONS

US 8,231,638 B2, 07/2012, Swarup et al. (withdrawn)

*Primary Examiner* — Michael T Rozanski

(57) ABSTRACT

A surgical robot system includes a surgical robot, a robot arm connected to such surgical robot, and an end-effector connected to the robot arm. A registration fixture is used in conjunction with various registration systems in the surgical robot system. Such registration systems likewise include a detachable base in the form of a detachable dynamic reference base, along with an associated mount, the dynamic reference base and mount having certain features which permit the dynamic reference base to be selectively attached, detached, and reattached at different phases of an operation, whether pre-operative or intra-operative, and such successive attachments are done without the dynamic reference base, and tracking markers associated therewith, losing registration. Related methods allow for the more efficient
(Continued)

and effective performance of operations by virtue of the dynamic reference base maintaining its registration during attachments and reattachments.

8 Claims, 27 Drawing Sheets

Related U.S. Application Data of application No. 16/737,029, filed on Jan. 8, 2020, now Pat. No. 11,571,265, which is a continuation-in-part of application No. 16/452,737, filed on Jun. 26, 2019, now Pat. No. 11,317,978, which is a continuation-in-part of application No. 16/361,863, filed on Mar. 22, 2019, now abandoned.

(51) Int. Cl.
    *A61B 90/00*        (2016.01)
    *A61B 90/10*        (2016.01)
    *A61B 90/14*        (2016.01)

(58) Field of Classification Search
    CPC ...... A61B 2090/363; A61B 2090/3762; A61B 2090/3954; A61B 2090/3966; A61B 2090/3983; A61B 34/30; A61B 90/11; A61B 90/14
    See application file for complete search history.

(56)                References Cited

U.S. PATENT DOCUMENTS

| | | | |
|---|---|---|---|
| 4,638,798 A | 1/1987 | Shelden et al. |
| 4,706,665 A | 11/1987 | Gouda |
| 5,078,140 A | 1/1992 | Kwoh |
| 5,116,344 A | 5/1992 | Sundqvist |
| 5,176,689 A | 1/1993 | Hardy et al. |
| 5,246,010 A | 9/1993 | Gazzara et al. |
| 5,354,314 A | 10/1994 | Hardy et al. |
| 5,397,323 A | 3/1995 | Taylor et al. |
| 5,423,832 A | 6/1995 | Gildenberg |
| 5,598,453 A | 1/1997 | Baba et al. |
| 5,647,373 A | 7/1997 | Paltieli |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,200,274 B1 | 3/2001 | McNeirney |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,298,262 B1 | 10/2001 | Franck et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,463,319 B1 | 10/2002 | Bucholz |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,529,765 B1 | 3/2003 | Franck |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,609,022 B2 | 8/2003 | Vilsmeier et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,694,162 B2 | 2/2004 | Hartlep |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,859,660 B2 | 2/2005 | Vilsmeier |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,206,626 B2 | 4/2007 | Quaid, III |
| 7,206,627 B2 | 4/2007 | Abovitz et al. |

(56)     References Cited

U.S. PATENT DOCUMENTS

| | | | |
|---|---|---|---|
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,616,735 B2 | 11/2009 | Maciunas et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,747,311 B2 | 6/2010 | Quaid, III |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,292 B2 | 11/2010 | Quaid et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,328 B2 | 4/2011 | Urquhart et al. |
| 7,925,653 B2 | 4/2011 | Saptharishi |
| 7,930,065 B2 | 4/2011 | Larkin et al. |
| 7,935,130 B2 | 5/2011 | Willliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,010,180 B2 | 8/2011 | Quaid et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,095,200 B2 | 1/2012 | Quaid, III |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |

(56) References Cited

U.S. PATENT DOCUMENTS

| | | | |
|---|---|---|---|
| 8,228,368 B2 | 7/2012 | Zhao et al. |
| 8,231,610 B2 | 7/2012 | Jo et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,263,933 B2 | 9/2012 | Zeile |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,503,759 B2 | 8/2013 | Greer et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,509,503 B2 | 8/2013 | Nahum et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Greer et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,263 B1 | 6/2014 | Rahimian et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |

(56) References Cited

U.S. PATENT DOCUMENTS

| | | |
|---|---|---|
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,911,499 B2 | 12/2014 | Quaid et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,237,861 B2 | 1/2016 | Nahum et al. |
| 9,308,050 B2 | 4/2016 | Kostrzewski et al. |
| 9,326,823 B2 | 5/2016 | McMillan et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,463,073 B2 | 10/2016 | Gill et al. |
| 9,492,235 B2 | 11/2016 | Hourtash et al. |
| 9,492,241 B2 | 11/2016 | Joskowiz et al. |
| 9,521,966 B2 | 12/2016 | Schwartz |
| 9,592,096 B2 | 3/2017 | Maillet et al. |
| 9,636,185 B2 | 5/2017 | Quaid et al. |
| 9,649,168 B2 | 5/2017 | Rahimian et al. |
| 9,750,432 B2 | 9/2017 | Nahum et al. |
| 9,750,465 B2 | 9/2017 | Engel et al. |
| 9,755,682 B2 | 9/2017 | Byler |
| 9,757,203 B2 | 9/2017 | Hourtash et al. |
| 9,788,906 B2 | 10/2017 | Piron et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,827,053 B2 | 11/2017 | Chen et al. |
| 9,833,254 B1 | 12/2017 | Barral et al. |
| 9,833,265 B2 | 12/2017 | Donner et al. |
| 9,844,414 B2 | 12/2017 | Fischer et al. |
| 9,848,922 B2 | 12/2017 | Tohmeh et al. |
| 9,925,011 B2 | 3/2018 | Gombert et al. |
| 9,925,013 B2 | 3/2018 | Dell et al. |
| 9,931,025 B1 | 4/2018 | Graetzel et al. |
| 10,034,717 B2 | 7/2018 | Miller et al. |
| 10,039,476 B2 | 8/2018 | Nahum et al. |
| 10,039,507 B2 | 8/2018 | Patil et al. |
| 10,070,940 B2 | 9/2018 | Bailey et al. |
| 10,123,841 B2 | 11/2018 | Kim et al. |
| 10,499,974 B2 | 12/2019 | Heim et al. |
| 10,639,111 B2 | 5/2020 | Kopp |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0119663 A1 | 6/2005 | Keyer et al. |
| 2005/0143651 A1 | 6/2005 | Verard et al. |
| 2005/0171558 A1 | 8/2005 | Abovitz et al. |
| 2005/0281385 A1 | 12/2005 | Johnson et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0118742 A1 | 5/2009 | Hartmann et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0294828 A1 | 11/2010 | Bindra et al. |
| 2010/0298704 A1 | 11/2010 | Pelissier et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0190832 A1 | 8/2011 | Taylor et al. |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306986 A1 | 12/2011 | Lee et al. |

(56) References Cited

U.S. PATENT DOCUMENTS

| | | |
|---|---|---|
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0123417 A1 | 5/2012 | Smith |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0190965 A1 | 7/2012 | Schaerer et al. |
| 2012/0190966 A1 | 7/2012 | Schaerer et al. |
| 2012/0197182 A1 | 8/2012 | Millman et al. |
| 2012/0201421 A1 | 8/2012 | Hartmann et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0130810 A1 | 5/2014 | Azizian et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0296871 A1 | 10/2014 | Chen et al. |
| 2014/0299648 A1 | 10/2014 | Shelton, IV et al. |
| 2014/0303434 A1 | 10/2014 | Farritor et al. |
| 2014/0303486 A1 | 10/2014 | Baumgartner et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0011866 A1 | 1/2015 | Baumgartner |
| 2015/0039034 A1 | 2/2015 | Frankel et al. |
| 2015/0073433 A1 | 3/2015 | Schaerer et al. |
| 2015/0085970 A1 | 3/2015 | Bouhnik et al. |
| 2015/0109427 A1 | 4/2015 | Wood et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0252940 A1 | 9/2015 | Goodwin et al. |
| 2015/0335390 A1 | 11/2015 | Gill |
| 2015/0335480 A1 | 11/2015 | Alvarez et al. |
| 2015/0342647 A1 | 12/2015 | Frankel et al. |
| 2015/0351860 A1 | 12/2015 | Piron et al. |
| 2016/0005194 A1 | 1/2016 | Schretter et al. |
| 2016/0038253 A1 | 2/2016 | Piron et al. |
| 2016/0058513 A1 | 3/2016 | Giorgi |
| 2016/0166329 A1 | 6/2016 | Langan et al. |
| 2016/0220320 A1 | 8/2016 | Crawford et al. |
| 2016/0235480 A1 | 8/2016 | Scholl et al. |
| 2016/0249990 A1 | 9/2016 | Glozman et al. |
| 2016/0278870 A1 | 9/2016 | Quaid et al. |
| 2016/0296293 A1 | 10/2016 | Gill et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |

(56) References Cited

U.S. PATENT DOCUMENTS

| | | |
|---|---|---|
| 2017/0156805 A1 | 6/2017 | Taylor et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0224358 A1 | 8/2017 | Kostrzewski |
| 2017/0231710 A1 | 8/2017 | Scholl et al. |
| 2017/0258426 A1 | 9/2017 | Risher-Kelly et al. |
| 2017/0265943 A1 | 9/2017 | Sela et al. |
| 2017/0265947 A1 | 9/2017 | Dyer et al. |
| 2017/0273748 A1 | 9/2017 | Hourtash et al. |
| 2017/0296277 A1 | 10/2017 | Hourtash et al. |
| 2017/0319289 A1 | 11/2017 | Neff |
| 2017/0333056 A1 | 11/2017 | Ponzer et al. |
| 2017/0360493 A1 | 12/2017 | Zucher et al. |
| 2018/0014892 A1 | 1/2018 | Piron et al. |
| 2018/0049825 A1 | 2/2018 | Kwon et al. |
| 2018/0049826 A1 | 2/2018 | Fischer et al. |
| 2018/0049839 A1 | 2/2018 | Seong et al. |
| 2018/0071029 A1 | 3/2018 | Srimohanarajeh et al. |
| 2018/0116742 A1 | 5/2018 | Dell et al. |
| 2018/0228559 A1 | 8/2018 | Brierton et al. |
| 2018/0325610 A1 | 11/2018 | Cameron et al. |
| 2018/0368656 A1 | 12/2018 | Austin et al. |
| 2019/0008598 A1 | 1/2019 | Frimer et al. |
| 2019/0029765 A1 | 1/2019 | Crawford et al. |
| 2019/0167362 A1 | 6/2019 | Crawford et al. |
| 2019/0274765 A1 | 9/2019 | Crawford et al. |

FOREIGN PATENT DOCUMENTS

| | | |
|---|---|---|
| EP | 3241518 A2 | 11/2017 |
| EP | 3375399 A2 | 9/2018 |
| JP | 2007508117 A | 4/2007 |
| JP | 2010-269142 A | 12/2010 |
| JP | 2013517101 A | 5/2013 |
| JP | 2013154138 A | 8/2013 |
| JP | 2016-514562 A | 5/2016 |
| JP | 2016-539681 A | 12/2016 |
| JP | 2017514581 A | 6/2017 |
| JP | 2017-524483 A | 8/2017 |
| JP | 2017-205495 A | 11/2017 |
| JP | 2018011938 A | 1/2018 |
| JP | 2018079304 A | 5/2018 |
| JP | 2018110841 A | 7/2018 |
| JP | 2018-532465 A | 11/2018 |
| WO | 2017203531 A1 | 11/2017 |

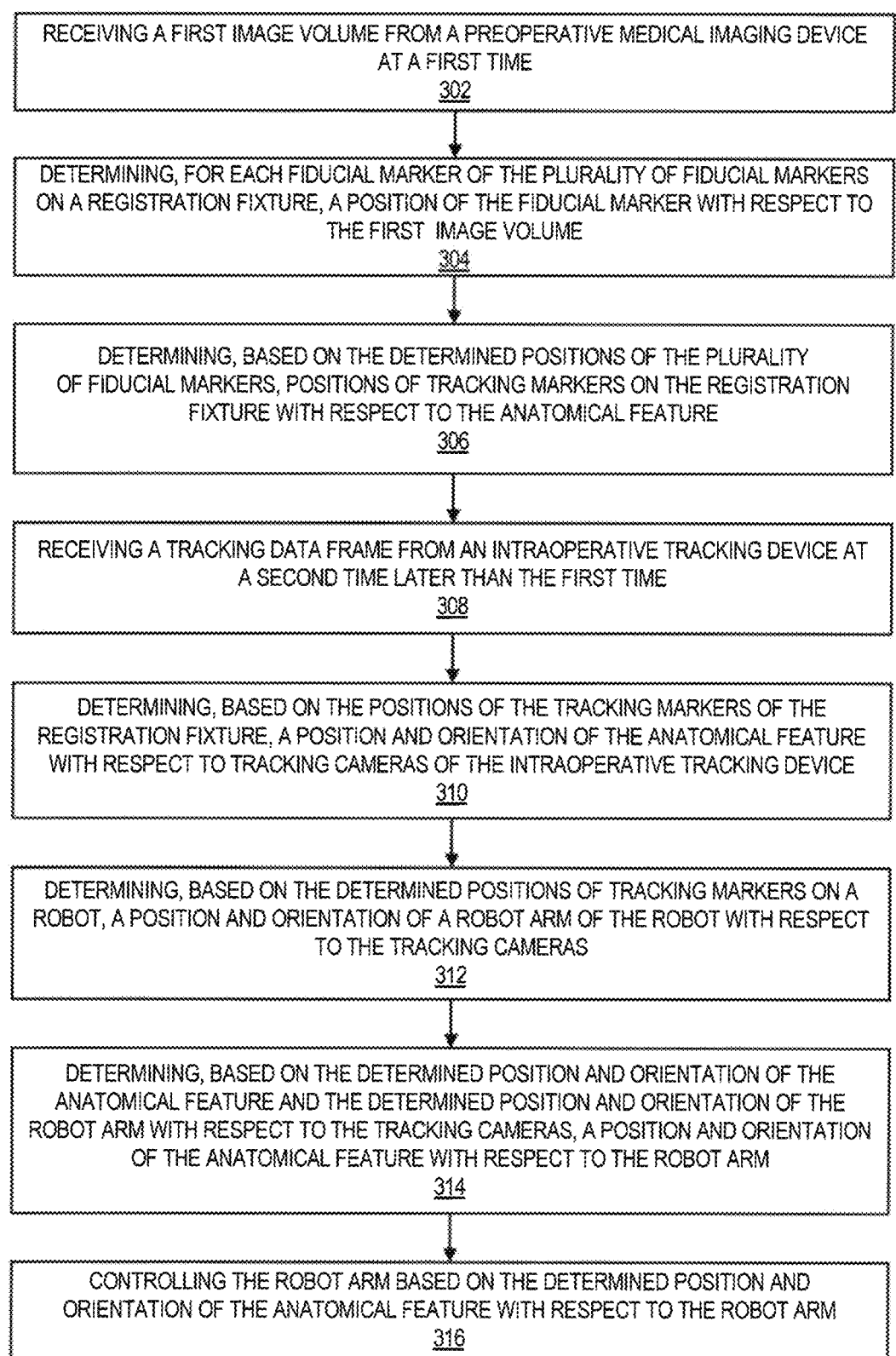

RECEIVING A FIRST IMAGE VOLUME FROM A PREOPERATIVE MEDICAL IMAGING DEVICE AT A FIRST TIME
302

DETERMINING, FOR EACH FIDUCIAL MARKER OF THE PLURALITY OF FIDUCIAL MARKERS ON A REGISTRATION FIXTURE, A POSITION OF THE FIDUCIAL MARKER WITH RESPECT TO THE FIRST IMAGE VOLUME
304

DETERMINING, BASED ON THE DETERMINED POSITIONS OF THE PLURALITY OF FIDUCIAL MARKERS, POSITIONS OF TRACKING MARKERS ON THE REGISTRATION FIXTURE WITH RESPECT TO THE ANATOMICAL FEATURE
306

RECEIVING A TRACKING DATA FRAME FROM AN INTRAOPERATIVE TRACKING DEVICE AT A SECOND TIME LATER THAN THE FIRST TIME
308

DETERMINING, BASED ON THE POSITIONS OF THE TRACKING MARKERS OF THE REGISTRATION FIXTURE, A POSITION AND ORIENTATION OF THE ANATOMICAL FEATURE WITH RESPECT TO TRACKING CAMERAS OF THE INTRAOPERATIVE TRACKING DEVICE
310

DETERMINING, BASED ON THE DETERMINED POSITIONS OF TRACKING MARKERS ON A ROBOT, A POSITION AND ORIENTATION OF A ROBOT ARM OF THE ROBOT WITH RESPECT TO THE TRACKING CAMERAS
312

DETERMINING, BASED ON THE DETERMINED POSITION AND ORIENTATION OF THE ANATOMICAL FEATURE AND THE DETERMINED POSITION AND ORIENTATION OF THE ROBOT ARM WITH RESPECT TO THE TRACKING CAMERAS, A POSITION AND ORIENTATION OF THE ANATOMICAL FEATURE WITH RESPECT TO THE ROBOT ARM
314

CONTROLLING THE ROBOT ARM BASED ON THE DETERMINED POSITION AND ORIENTATION OF THE ANATOMICAL FEATURE WITH RESPECT TO THE ROBOT ARM
316

FIG. 3

SYSTEM FOR NEURONAVIGATION REGISTRATION AND ROBOTIC TRAJECTORY GUIDANCE, ROBOTIC SURGERY, AND RELATED METHODS AND DEVICES

CROSS-REFERENCE TO RELATED APPLICATION

This application is a divisional application of U.S. patent application Ser. No. 18/150,527, filed Jan. 5, 2023 and published as U.S. 2023-0141953, which is a divisional application of U.S. patent application Ser. No. 16/737,029, filed Jan. 8, 2020 and now U.S. Pat. No. 11,571,265, which is a continuation-in-part of U.S. patent application Ser. No. 16/452,737, filed Jun. 26, 2019 and now U.S. Pat. No. 11,317,978, which is a continuation-in-part of U.S. patent application Ser. No. 16/361,863, filed Mar. 22, 2019 and published as U.S. 2020-0297426, the entire contents of each of which are hereby incorporated by reference in their entireties for all purposes.

FIELD

The present disclosure relates to medical devices and systems, and more particularly, systems for neuronavigation registration and robotic trajectory guidance, robotic surgery, and related methods and devices.

BACKGROUND

Position recognition systems for robot assisted surgeries are used to determine the position of and track a particular object in 3-dimensions (3D). In robot assisted surgeries, for example, certain objects, such as surgical instruments, need to be tracked with a high degree of precision as the instrument is being positioned and moved by a robot or by a physician, for example.

Position recognition systems may use passive and/or active sensors or markers for registering and tracking the positions of the objects. Using these sensors, the system may geometrically resolve the 3-dimensional position of the sensors based on information from or with respect to one or more cameras, signals, or sensors, etc. These surgical systems can therefore utilize position feedback to precisely guide movement of robotic arms and tools relative to a patients' surgical site. Thus, there is a need for a system that efficiently and accurately provides neuronavigation registration and robotic trajectory guidance in a surgical environment.

Position recognition systems for robot-assisted surgeries often make use of registration fixtures as part of the aforesaid neuronavigation registration, robotic trajectory guidance, or for still other positioning and related functions for robotic-assisted surgery. Tracking markers are likewise used by position recognition systems and/or associated registration fixtures, and it is often necessary to have the positions of such tracking markers determined, registered, or otherwise subject to processing for purposes of the position recognition systems, navigation, or robotic trajectory guidance. In certain implementations, dynamic reference bases, referred to, at times, as DRBs, may be associated with the position recognition systems, including registration fixtures, stereotactic frames, and the like, and the aforementioned tracking markers may likewise be associated with such DRBs.

It is thus advantageous for position determinations of tracking markers or registration fixtures, including DRBs, to be accomplished efficiently and accurately. Registrations of tracking markers generally involve position and orientation relative to one or more of the registration fixture, patient, or anatomy to be operated upon, and such registration may need to be determined or maintained pre-operatively and again intra-operatively.

The need to employ GPS-assisted or other navigation protocols dependent on tracking markers and position determinations likewise may not be optimized when DRBs and their related positioning systems fall out of registration, or otherwise require repetitive verifications, registrations, repositionings, and the like.

To the extent certain of the determinations are associated with a non-sterile environment whereas other determinations are associated with a sterile environment, the foregoing determinations of position or registration are further complicated.

SUMMARY

According to some implementations, a surgical robot system is configured for surgery on an anatomical feature of a patient, and includes a surgical robot, a robot arm connected to such surgical robot, and an end-effector connected to the robot arm. One of the registration fixtures as discussed herein is affixed or otherwise secured in position with respect to a patient whose anatomical feature is of interest for the associated surgical procedure. A plurality of tracking markers have positions which are likewise registered with respect to such registration fixture.

The robot system includes one or more suitable processor circuits having memory associated therewith and machine-readable instructions to be executed by suitable operations of the processor circuit.

The registration fixture, in certain implementations, includes a detachable base, such as a detachable dynamic reference base, and such detachable dynamic reference base has a plurality of tracking markers mounted thereto. A mount associated with the registration fixture and/or the detachable dynamic reference base is adapted so that, after the system determines the positions of the tracking markers, the detachable dynamic reference base ("DRB") may be reattached relative to the registration fixture or the robotic system and such reattachment is such that the tracking markers assume substantially the same positions as those previously determined positions of such tracking markers.

In still further implementations, the mount and detachable DRB are secured relative to each other by mounting members, with such mounting members having features to form a kinematic mount which operates to repeatedly attach the mount and the base at predetermined mating positions which vary by less than 15% between successive detachments and reattachments.

According to still further implementations, the mounting members may comprise mating pairs of contacts and receiving pins, with one contact on either the mount or the base and at least one receiving pin for engaging the contact on the other of the mount or the base.

In various additional implementations, a keyed flange, having mating or complementary portions on the detachable base and the mount, has features such that the base and mount are positionable in a single orientation. The keyed flange may take the form of a post extending from one of the opposing surfaces of the detachable base or the mount and a corresponding cut-out formed in the other of the detachable base or the mount, such cut-out being located to receive the post therein with little to no clearance, thereby assuring that the base and mount are positionable in such single orientation.

The mounting members may be in the form of a pair of cylindrical pins disposed on one of the opposing surfaces of the mount or the DRB, whereas the contacts on the other of the opposing surfaces may be in the form of hemispherical surfaces sized to engage opposing portions on each of the two pins of the respective pairs of pins.

The above-described system and its various features may be associated with a variety of related procedures or processes, collectively referred to herein as methods. One such method involves running a cranial procedure on a patient with a computer-implemented surgical robot of a corresponding robot system. The method involves establishing a sterile field; however, prior to establishing the sterile field, the patient is registered in the non-sterile field and incision points for the cranial procedure are marked. The registration of the patient includes performing a first, detachable mounting of a plurality of tracking markers in a first predetermined position and orientation relative to a patient registration fixture. After such mounting, a determination is made, by execution of suitable computer instructions, of a first position and first orientation for the tracking marker positions which correspond to the plurality of tracking markers. Thereafter, under this method, the plurality of tracking markers are detached from their previous mounting. After establishment of the sterile field, a second detachable mounting of the plurality of tracking markers is performed. During performance of the second detachable mounting, the tracking markers are prevented from being mounted other than in the first position and the first orientation.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings:

FIG. 3 is a flowchart diagram illustrating computer-implemented operations for determining a position and orientation of an anatomical feature of a patient with respect to a robot arm of a surgical robot, according to some embodiments;

DETAILED DESCRIPTION

Figure 1A:
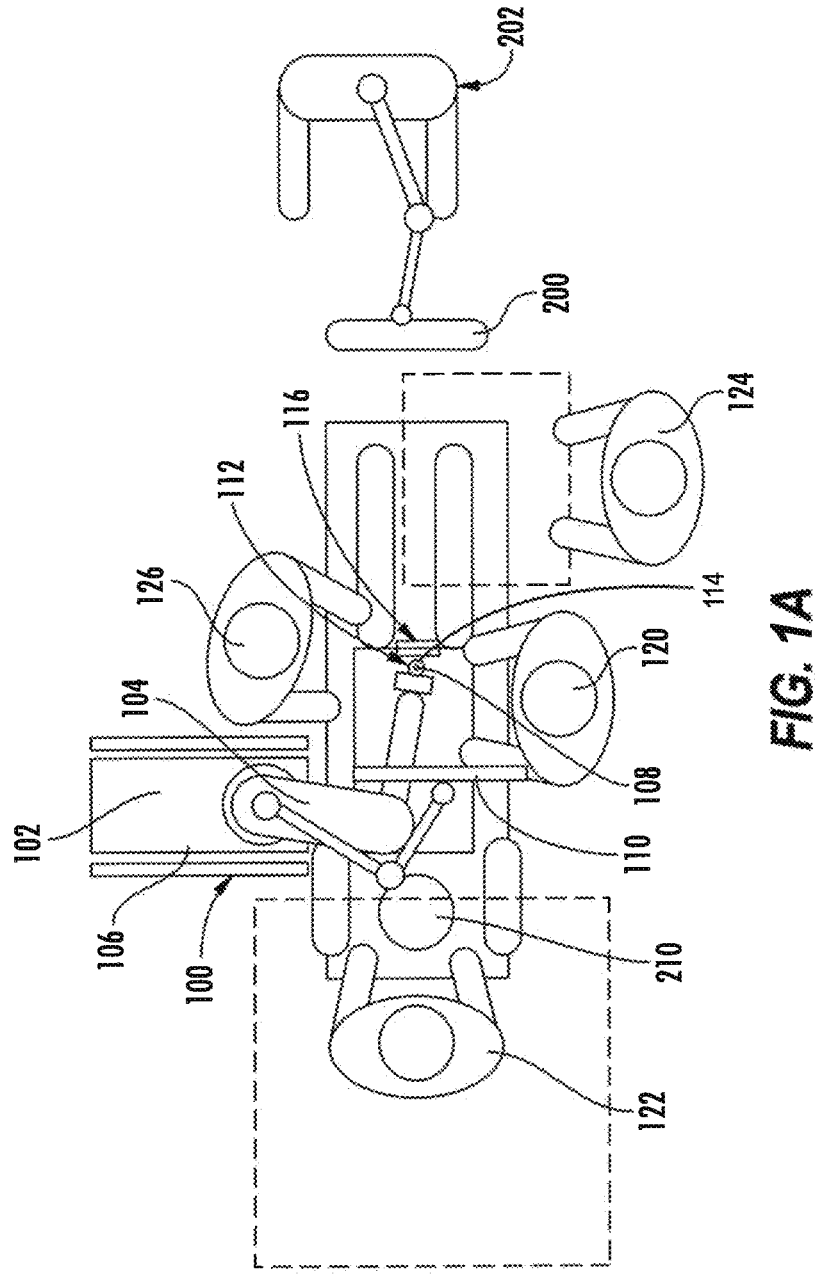
FIG. 1A is an overhead view of an arrangement for locations of a robotic system, patient, surgeon, and other medical personnel during a surgical procedure, according to some embodiments.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

According to some other embodiments, systems for neuronavigation registration and robotic trajectory guidance, and related methods and devices are disclosed. In some embodiments, a first image having an anatomical feature of a patient, a registration fixture that is fixed with respect to the anatomical feature of the patient, and a first plurality of fiducial markers that are fixed with respect to the registration fixture is analyzed, and a position is determined for each fiducial marker of the first plurality of fiducial markers. Next, based on the determined positions of the first plurality of fiducial markers, a position and orientation of the registration fixture with respect to the anatomical feature is determined. A data frame comprising a second plurality of tracking markers that are fixed with respect to the registration fixture is also analyzed, and a position is determined for each tracking marker of the second plurality of tracking markers. Based on the determined positions of the second plurality of tracking markers, a position and orientation of the registration fixture with respect to a robot arm of a surgical robot is determined. Based on the determined position and orientation of the registration fixture with respect to the anatomical feature and the determined position and orientation of the registration fixture with respect to the robot arm, a position and orientation of the anatomical feature with respect to the robot arm is determined, which allows the robot arm to be controlled based on the determined position and orientation of the anatomical feature with respect to the robot arm.

Advantages of this and other embodiments include the ability to combine neuronavigation and robotic trajectory alignment into one system, with support for a wide variety of different registration hardware and methods. For example, as will be described in detail below, embodiments may support both computerized tomography (CT) and fluoroscopy (fluoro) registration techniques, and may utilize frame-based and/or frameless surgical arrangements. Moreover, in many embodiments, if an initial (e.g. preoperative) registration is compromised due to movement of a registration fixture, registration of the registration fixture (and of the anatomical feature by extension) can be re-established intra-operatively without suspending surgery and re-capturing preoperative images.

Referring now to the drawings, FIG. 1A illustrates a surgical robot system 100 in accordance with an embodiment. Surgical robot system 100 may include, for example, a surgical robot 102, one or more robot arms 104, a base 106, a display 110, an end-effector 112, for example, including a guide tube 114, and one or more tracking markers 118. The robot arm 104 may be movable along and/or about an axis relative to the base 106, responsive to input from a user, commands received from a processing device, or other methods. The surgical robot system 100 may include a patient tracking device 116 also including one or more tracking markers 118, which is adapted to be secured directly to the patient 210 (e.g., to a bone of the patient 210). As will be discussed in greater detail below, the tracking markers 118 may be secured to or may be part of a stereotactic frame that is fixed with respect to an anatomical feature of the patient 210. The stereotactic frame may also be secured to a fixture to prevent movement of the patient 210 during surgery.

Figure 1B:
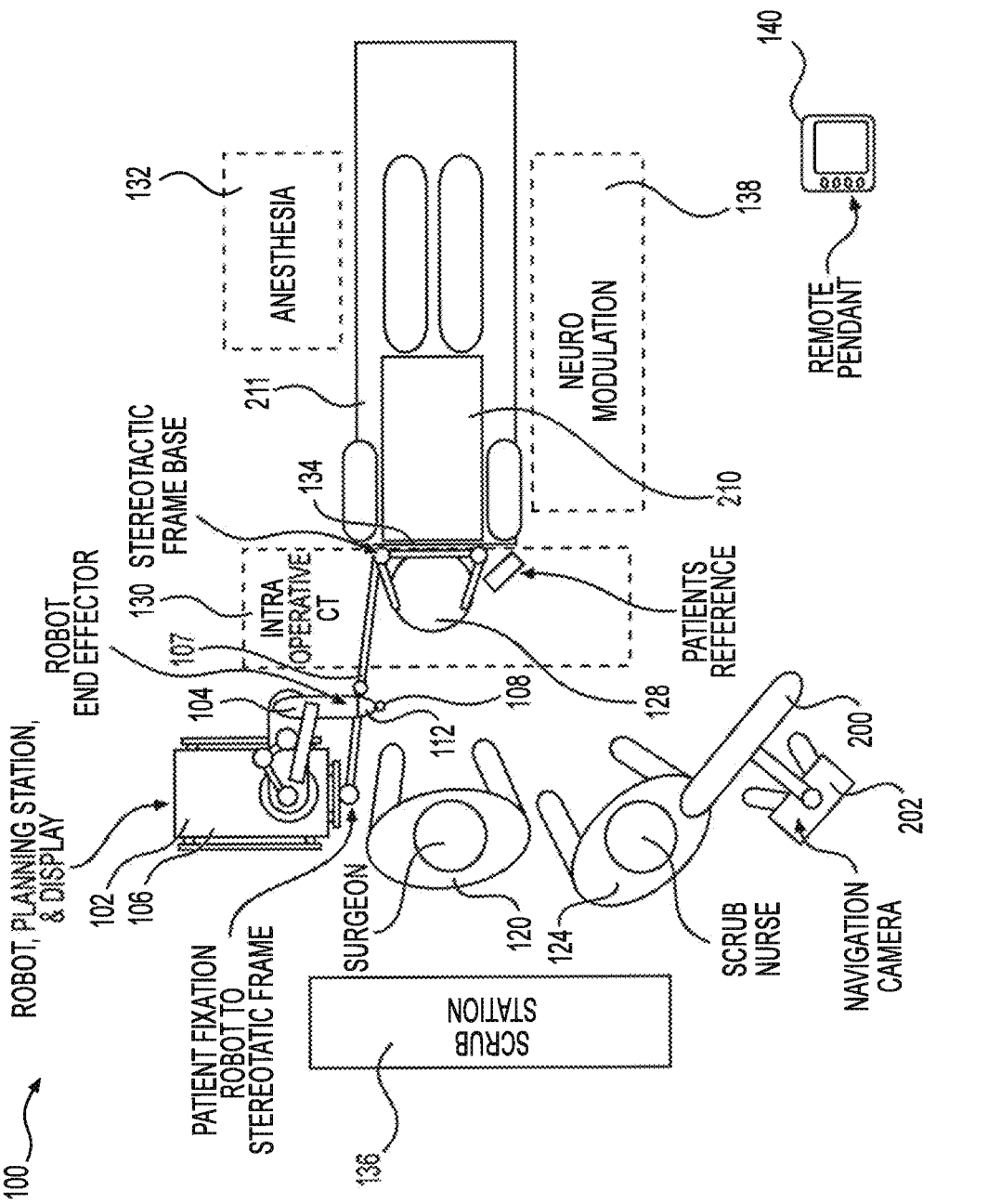
FIG. 1B is an overhead view of an alternate arrangement for locations of a robotic system, patient, surgeon, and other medical personnel during a cranial surgical procedure, according to some embodiments.

According to an alternative embodiment, FIG. 1B is an overhead view of an alternate arrangement for locations of a robotic system 100, patient 210, surgeon 120, and other medical personnel during a cranial surgical procedure. During a cranial procedure, for example, the robot 102 may be positioned behind the head 128 of the patient 210. The robot arm 104 of the robot 102 has an end-effector 112 that may hold a surgical instrument 108 during the procedure. In this example, a stereotactic frame 134 is fixed with respect to the patient's head 128, and the patient 210 and/or stereotactic frame 134 may also be secured to a patient base 211 to prevent movement of the patient's head 128 with respect to the patient base 211. In addition, the patient 210, the stereotactic frame 134 and/or or the patient base 211 may be secured to the robot base 106, such as via an auxiliary arm 107, to prevent relative movement of the patient 210 with respect to components of the robot 102 during surgery. Different devices may be positioned with respect to the patient's head 128 and/or patient base 211 as desired to facilitate the procedure, such as an intra-operative CT device 130, an anesthesiology station 132, a scrub station 136, a neuro-modulation station 138, and/or one or more remote pendants 140 for controlling the robot 102 and/or other devices or systems during the procedure.

Figure 2:
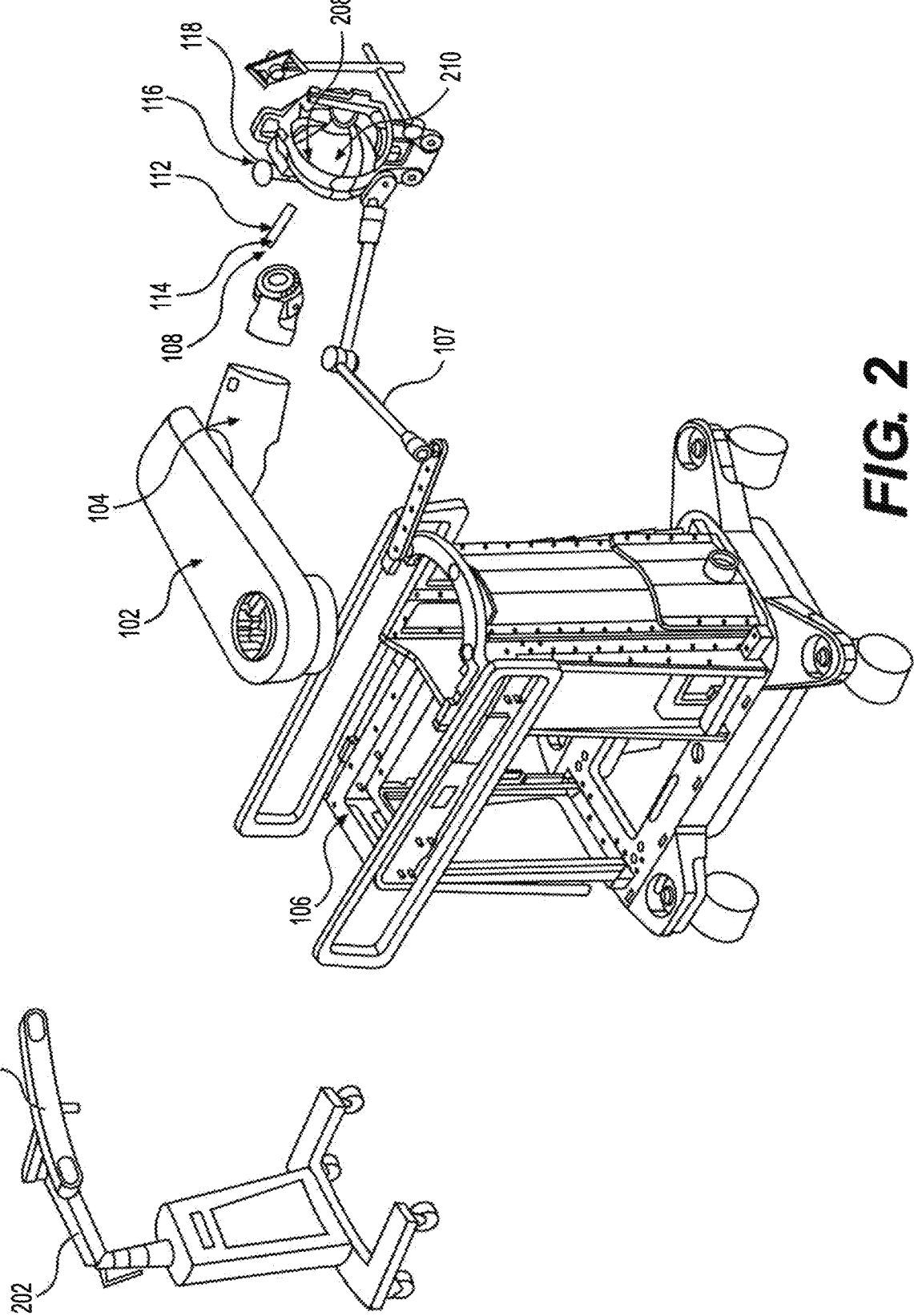
FIG. 2 illustrates a robotic system including positioning of the surgical robot and a camera relative to the patient according to some embodiments.

The surgical robot system 100 in the examples of FIGS. 1A and/or 1B may also use a sensor, such as a camera 200, for example, positioned on a camera stand 202. The camera stand 202 can have any suitable configuration to move, orient, and support the camera 200 in a desired position. The camera 200 may include any suitable camera or cameras, such as one or more cameras (e.g., bifocal or stereophotogrammetric cameras), able to identify, for example, active or passive tracking markers 118 (shown as part of patient tracking device 116 in FIG. 2) in a given measurement volume viewable from the perspective of the camera 200. In this example, the camera 200 may scan the given measurement volume and detect the light that comes from the tracking markers 118 in order to identify and determine the position of the tracking markers 118 in three-dimensions. For example, active tracking markers 118 may include infrared-emitting markers that are activated by an electrical signal (e.g., infrared light emitting diodes (LEDs)), and/or passive tracking markers 118 may include retro-reflective markers that reflect infrared or other light (e.g., they reflect incoming IR radiation into the direction of the incoming light), for example, emitted by illuminators on the camera 200 or other suitable sensor or other device.

In many surgical procedures, one or more targets of surgical interest, such as targets within the brain for example, are localized to an external reference frame. For example, stereotactic neurosurgery may use an externally mounted stereotactic frame that facilitates patient localization and implant insertion via a frame mounted arc. Neuro-navigation is used to register, e.g., map, targets within the brain based on pre-operative or intraoperative imaging. Using this pre-operative or intraoperative imaging, links and associations can be made between the imaging and the actual anatomical structures in a surgical environment, and these links and associations can be utilized by robotic trajectory systems during surgery.

According to some embodiments, various software and hardware elements may be combined to create a system that can be used to plan, register, place and verify the location of an instrument or implant in the brain. These systems may integrate a surgical robot, such as the surgical robot 102 of FIGS. 1A and/or 1B, and may employ a surgical navigation system and planning software to program and control the surgical robot. In addition or alternatively, the surgical robot 102 may be remotely controlled, such as by nonsterile personnel.

The robot 102 may be positioned near or next to patient 210, and it will be appreciated that the robot 102 can be positioned at any suitable location near the patient 210 depending on the area of the patient 210 undergoing the operation. The camera 200 may be separated from the surgical robot system 100 and positioned near or next to patient 210 as well, in any suitable position that allows the camera 200 to have a direct visual line of sight to the surgical field 208. In the configuration shown, the surgeon 120 may be positioned across from the robot 102, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 may remain unimpeded by the locations of the robot 102 and camera 200.

With respect to the other components of the robot 102, the display 110 can be attached to the surgical robot 102 and in other embodiments, the display 110 can be detached from surgical robot 102, either within a surgical room with the surgical robot 102, or in a remote location. The end-effector 112 may be coupled to the robot arm 104 and controlled by at least one motor. In some embodiments, end-effector 112 can comprise a guide tube 114, which is able to receive and orient a surgical instrument 108 used to perform surgery on the patient 210. As used herein, the term "end-effector" is used interchangeably with the terms "end-effectuator" and "effectuator element." Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument 108 in a desired manner.

The surgical robot 102 is able to control the translation and orientation of the end-effector 112. The robot 102 is able to move end-effector 112 along x-, y-, and z-axes, for example. The end-effector 112 can be configured for selective rotation about one or more of the x-, y-, and z-axis such that one or more of the Euler Angles (e.g., roll, pitch, and/or yaw) associated with end-effector 112 can be selectively controlled. In some embodiments, selective control of the translation and orientation of end-effector 112 can permit performance of medical procedures with significantly improved accuracy compared to conventional robots that use, for example, a six degree of freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some embodiments, the position of the surgical instrument 108 can be dynamically updated so that surgical robot 102 can be aware of the location of the surgical instrument 108 at all times during the procedure. Consequently, in some embodiments, surgical robot 102 can move the surgical instrument 108 to the desired position quickly without any further assistance from a physician (unless the physician so desires). In some further embodiments, surgical robot 102 can be configured to correct the path of the surgical instrument 108 if the surgical instrument 108 strays from the selected, preplanned trajectory. In some embodiments, surgical robot 102 can be configured to permit stoppage, modification, and/or manual control of the movement of end-effector 112 and/or the surgical instrument 108. Thus, in use, in some embodiments, a physician or other user can operate the system 100, and has the option to stop, modify, or manually control the autonomous movement of end-effector 112 and/or the surgical instrument 108. Further details of surgical robot system 100 including the control and movement of a surgical instrument 108 by surgical robot 102 can be found in co-pending U.S. Patent Publication No. 2013/0345718, which is incorporated herein by reference in its entirety.

As will be described in greater detail below, the surgical robot system 100 can comprise one or more tracking markers configured to track the movement of robot arm 104, end-effector 112, patient 210, and/or the surgical instrument 108 in three dimensions. In some embodiments, a plurality of tracking markers can be mounted (or otherwise secured) thereon to an outer surface of the robot 102, such as, for example and without limitation, on base 106 of robot 102, on robot arm 104, and/or on the end-effector 112. In some embodiments, such as the embodiment of FIG. 3 below, for example, one or more tracking markers can be mounted or otherwise secured to the end-effector 112. One or more tracking markers can further be mounted (or otherwise secured) to the patient 210. In some embodiments, the plurality of tracking markers can be positioned on the patient 210 spaced apart from the surgical field 208 to reduce the likelihood of being obscured by the surgeon, surgical tools, or other parts of the robot 102. Further, one or more tracking markers can be further mounted (or otherwise secured) to the surgical instruments 108 (e.g., a screw driver, dilator, implant inserter, or the like). Thus, the tracking markers enable each of the marked objects (e.g., the end-effector 112, the patient 210, and the surgical instruments 108) to be tracked by the surgical robot system 100. In some embodiments, system 100 can use tracking information collected from each of the marked objects to calculate the orientation and location, for example, of the end-effector 112, the surgical instrument 108 (e.g., positioned in the tube 114 of the end-effector 112), and the relative position of the patient 210. Further details of surgical robot system 100 including the control, movement and tracking of surgical robot 102 and of a surgical instrument 108 can be found in U.S. Patent Publication No. 2016/0242849, which is incorporated herein by reference in its entirety.

In some embodiments, pre-operative imaging may be used to identify the anatomy to be targeted in the procedure. If desired by the surgeon the planning package will allow for the definition of a reformatted coordinate system. This reformatted coordinate system will have coordinate axes anchored to specific anatomical landmarks, such as the anterior commissure (AC) and posterior commissure (PC) for neurosurgery procedures. In some embodiments, multiple pre-operative exam images (e.g., CT or magnetic resonance (MR) images) may be co-registered such that it is possible to transform coordinates of any given point on the anatomy to the corresponding point on all other pre-operative exam images.

As used herein, registration is the process of determining the coordinate transformations from one coordinate system to another. For example, in the co-registration of preoperative images, co-registering a CT scan to an MR scan means that it is possible to transform the coordinates of an anatomical point from the CT scan to the corresponding anatomical location in the MR scan. It may also be advantageous to register at least one exam image coordinate system to the coordinate system of a common registration fixture, such as a dynamic reference base (DRB), which may allow the camera 200 to keep track of the position of the patient in the camera space in real-time so that any intraoperative movement of an anatomical point on the patient in the room can be detected by the robot system 100 and accounted for by compensatory movement of the surgical robot 102.

FIG. 3 is a flowchart diagram illustrating computer-implemented operations 300 for determining a position and orientation of an anatomical feature of a patient with respect to a robot arm of a surgical robot, according to some embodiments. The operations 300 may include receiving a first image volume, such as a CT scan, from a preoperative image capture device at a first time (Block 302). The first image volume includes an anatomical feature of a patient and at least a portion of a registration fixture that is fixed with respect to the anatomical feature of the patient. The registration fixture includes a first plurality of fiducial markers that are fixed with respect to the registration fixture. The operations 300 further include determining, for each fiducial marker of the first plurality of fiducial markers, a position of the fiducial marker relative to the first image volume (Block 304). The operations 300 further include, determining, based on the determined positions of the first plurality of fiducial markers, positions of an array of tracking markers on the registration fixture (fiducial registration array or FRA) with respect to the anatomical feature (Block 306).

The operations 300 may further include receiving a tracking data frame from an intraoperative tracking device comprising a plurality of tracking cameras at a second time that is later than the first time (Block 308). The tracking frame includes positions of a plurality of tracking markers that are fixed with respect to the registration fixture (FRA) and a plurality of tracking markers that are fixed with respect to the robot. The operations 300 further include determining, for based on the positions of tracking markers of the registration fixture, a position and orientation of the anatomical feature with respect to the tracking cameras (Block 310). The operations 300 further include determining, based on the determined positions of the plurality of tracking markers on the robot, a position and orientation of the robot arm of a surgical robot with respect to the tracking cameras (Block 312).

The operations 300 further include determining, based on the determined position and orientation of the anatomical feature with respect to the tracking cameras and the determined position and orientation of the robot arm with respect to the tracking cameras, a position and orientation of the anatomical feature with respect to the robot arm (Block 314). The operations 300 further include controlling movement of the robot arm with respect to the anatomical feature, e.g., along and/or rotationally about one or more defined axis, based on the determined position and orientation of the anatomical feature with respect to the robot arm (Block 316).

Figure 4:
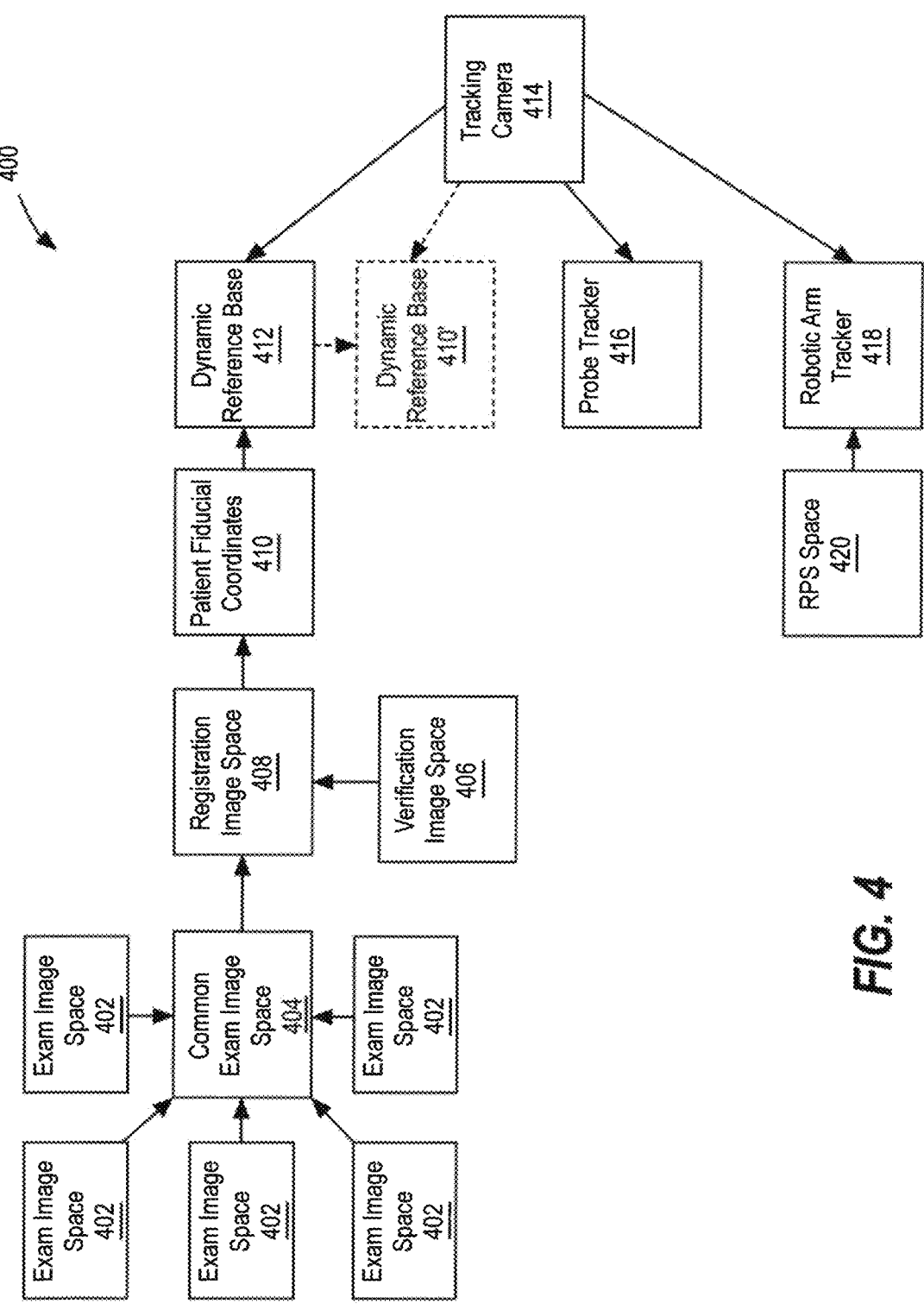
FIG. 4 is a diagram illustrating processing of data for determining a position and orientation of an anatomical feature of a patient with respect to a robot arm of a surgical robot, according to some embodiments.

FIG. 4 is a diagram illustrating a data flow 400 for a multiple coordinate transformation system, to enable determining a position and orientation of an anatomical feature of a patient with respect to a robot arm of a surgical robot, according to some embodiments. In this example, data from a plurality of exam image spaces 402, based on a plurality of exam images, may be transformed and combined into a common exam image space 404. The data from the common exam image space 404 and data from a verification image space 406, based on a verification image, may be transformed and combined into a registration image space 408. Data from the registration image space 408 may be transformed into patient fiducial coordinates 410, which is transformed into coordinates for a DRB 412. A tracking camera 414 may detect movement of the DRB 412 (represented by DRB 412') and may also detect a location of a probe tracker 416 to track coordinates of the DRB 412 over time. A robotic arm tracker 418 determines coordinates for the robot arm based on transformation data from a Robotics Planning System (RPS) space 420 or similar modeling system, and/or transformation data from the tracking camera 414.

It should be understood that these and other features may be used and combined in different ways to achieve registration of image space, i.e., coordinates from image volume, into tracking space, i.e., coordinates for use by the surgical robot in real-time. As will be discussed in detail below, these features may include fiducial-based registration such as stereotactic frames with CT localizer, preoperative CT or MRI registered using intraoperative fluoroscopy, calibrated scanner registration where any acquired scan's coordinates are pre-calibrated relative to the tracking space, and/or surface registration using a tracked probe, for example.

Figure 5A:
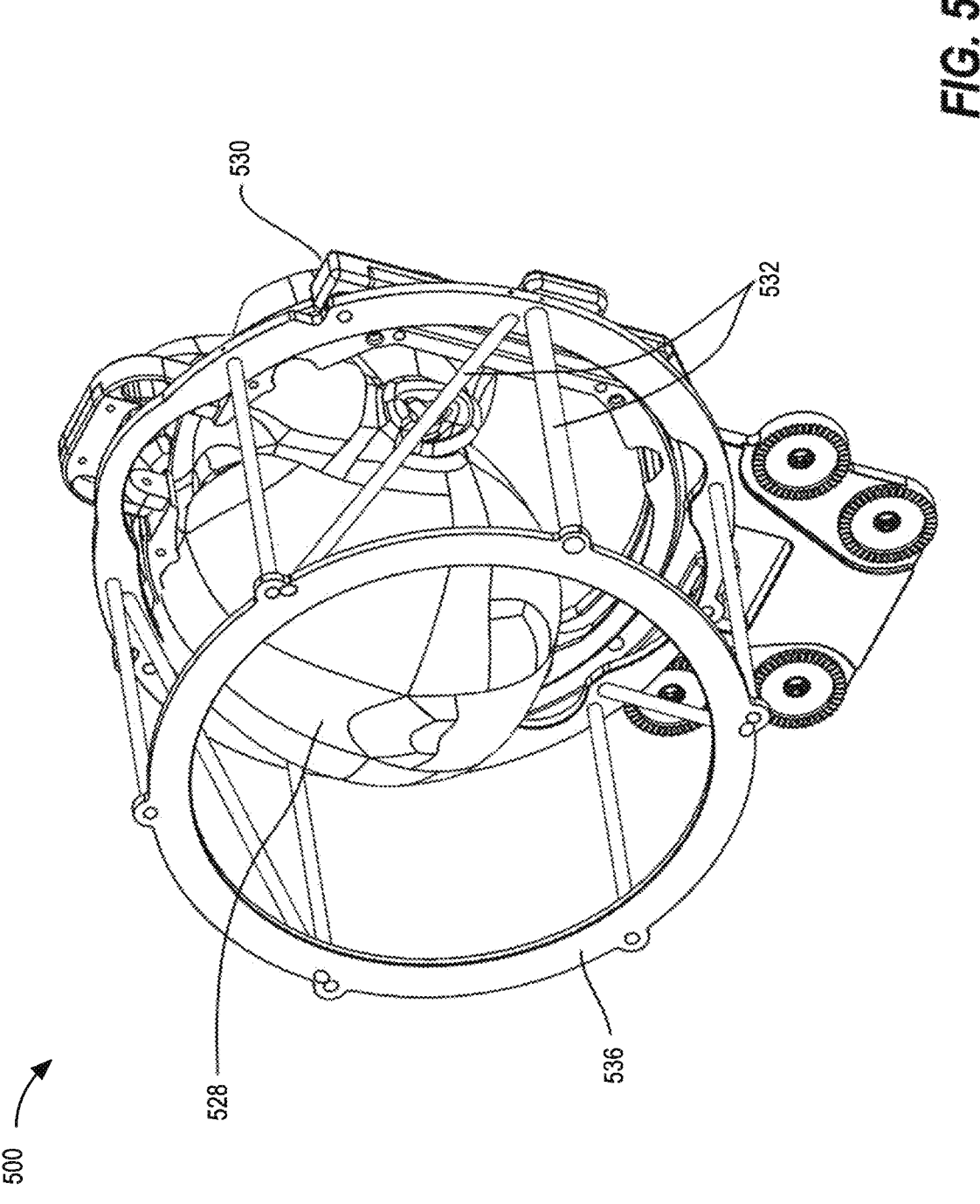
FIGS. 5A-5C illustrate a system for registering an anatomical feature of a patient using a computerized tomography (CT) localizer, a frame reference array (FRA), and a dynamic reference base (DRB), according to some embodiments.
Figure 5B:
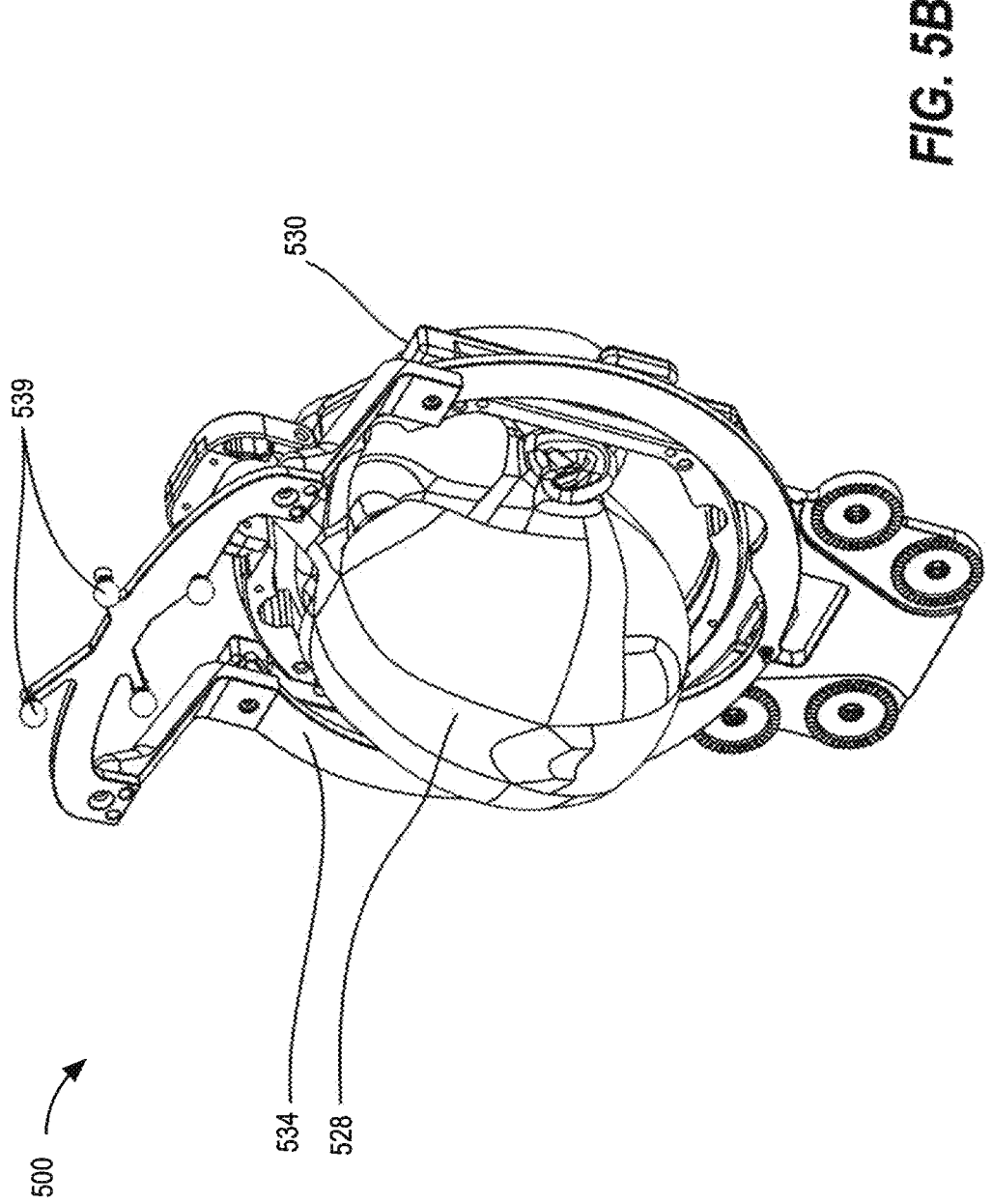
Figure 5C:
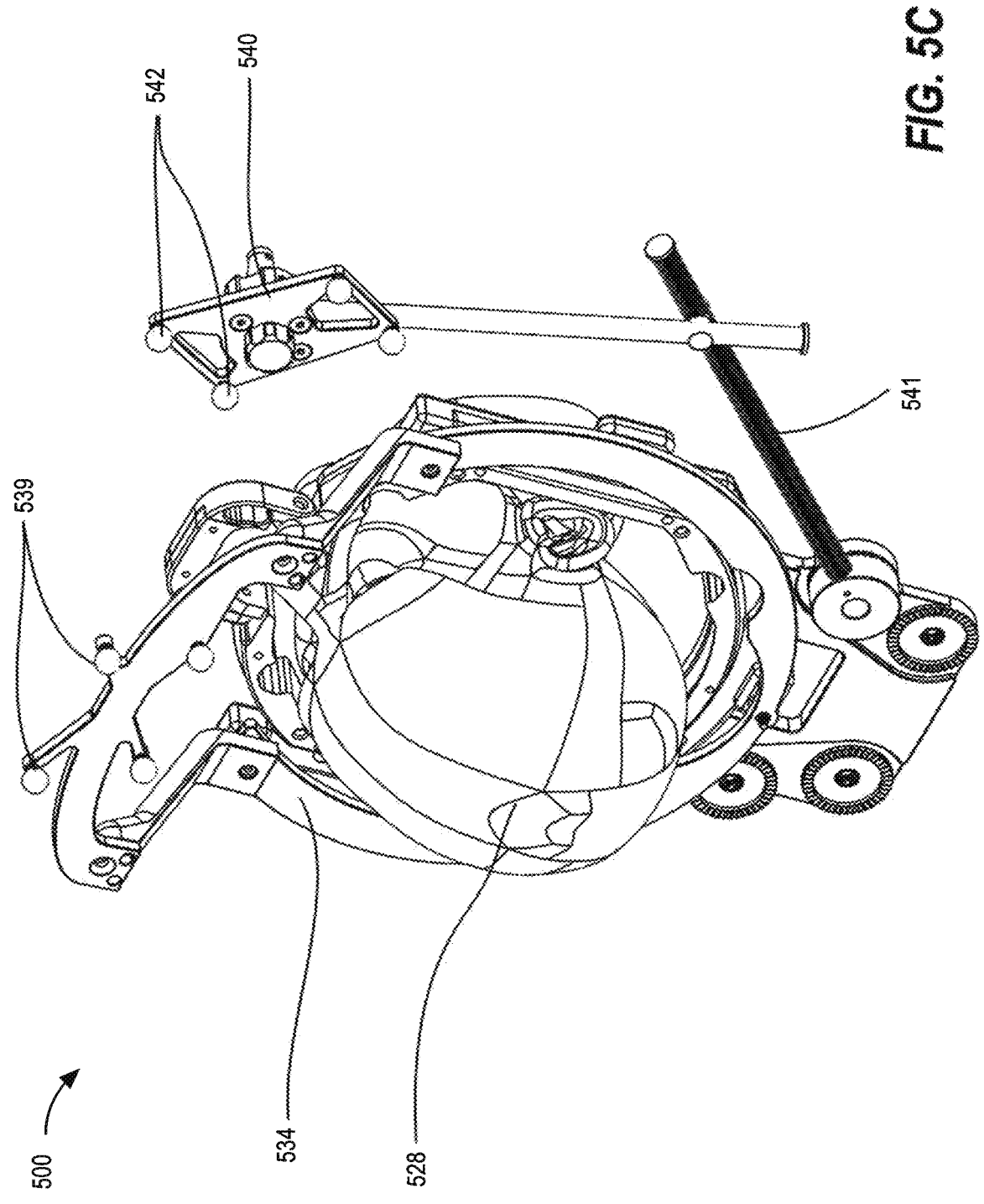

In one example, FIGS. 5A-5C illustrate a system 500 for registering an anatomical feature of a patient. In this example, the stereotactic frame base 530 is fixed to an anatomical feature 528 of patient, e.g., the patient's head. As shown by FIG. 5A, the stereotactic frame base 530 may be affixed to the patient's head 528 prior to registration using pins clamping the skull or other method. The stereotactic frame base 530 may act as both a fixation platform, for holding the patient's head 528 in a fixed position, and registration and tracking platform, for alternatingly holding the CT localizer 536 or the FRA fixture 534. The CT localizer 536 includes a plurality of fiducial markers 532 (e.g., N-pattern radio-opaque rods or other fiducials), which are automatically detected in the image space using image processing. Due to the precise attachment mechanism of the CT localizer 536 to the base 530, these fiducial markers 532 are in known space relative to the stereotactic frame base 530. A 3D CT scan of the patient with CT localizer 536 attached is taken, with an image volume that includes both the patient's head 528 and the fiducial markers 532 of the CT localizer 536. This registration image can be taken intraoperatively or preoperatively, either in the operating room or in radiology, for example. The captured 3D image dataset is stored to computer memory.

As shown by FIG. 5B, after the registration image is captured, the CT localizer 536 is removed from the stereotactic frame base 530 and the frame reference array fixture 534 is attached to the stereotactic frame base 530. The stereotactic frame base 530 remains fixed to the patient's head 528, however, and is used to secure the patient during surgery, and serves as the attachment point of a frame reference array fixture 534. The frame reference array fixture 534 includes a frame reference array (FRA), which is a rigid array of three or more tracked markers 539, which may be the primary reference for optical tracking. By positioning the tracked markers 539 of the FRA in a fixed, known location and orientation relative to the stereotactic frame base 530, the position and orientation of the patient's head 528 may be tracked in real time. Mount points on the FRA fixture 534 and stereotactic frame base 530 may be designed such that the FRA fixture 534 attaches reproducibly to the stereotactic frame base 530 with minimal (i.e., submillimetric) variability. These mount points on the stereotactic frame base 530 can be the same mount points used by the CT localizer 536, which is removed after the scan has been taken. An auxiliary arm (such as auxiliary arm 107 of FIG. 1B, for example) or other attachment mechanism can also be used to securely affix the patient to the robot base to ensure that the robot base is not allowed to move relative to the patient.

As shown by FIG. 5C, a dynamic reference base (DRB) 540 may also be attached to the stereotactic frame base 530. The DRB 540 in this example includes a rigid array of three or more tracked markers 542. In this example, the DRB 540 and/or other tracked markers may be attached to the stereotactic frame base 530 and/or to directly to the patient's head 528 using auxiliary mounting arms 541, pins, or other attachment mechanisms. Unlike the FRA fixture 534, which mounts in only one way for unambiguous localization of the stereotactic frame base 530, the DRB 540 in general may be attached as needed for allowing unhindered surgical and equipment access. Once the DRB 540 and FRA fixture 534 are attached, registration, which was initially related to the tracking markers 539 of the FRA, can be optionally transferred or related to the tracking markers 542 of the DRB 540. For example, if any part of the FRA fixture 534 blocks surgical access, the surgeon may remove the FRA fixture 534 and navigate using only the DRB 540. However, if the FRA fixture 534 is not in the way of the surgery, the surgeon could opt to navigate from the FRA markers 539, without using a DRB 540, or may navigate using both the FRA markers 539 and the DRB 540. In this example, the FRA fixture 534 and/or DRB 540 uses optical markers, the tracked positions of which are in known locations relative to the stereotactic frame base 530, similar to the CT localizer 536, but it should be understood that many other additional and/or alternative techniques may be used.

Figure 6A:
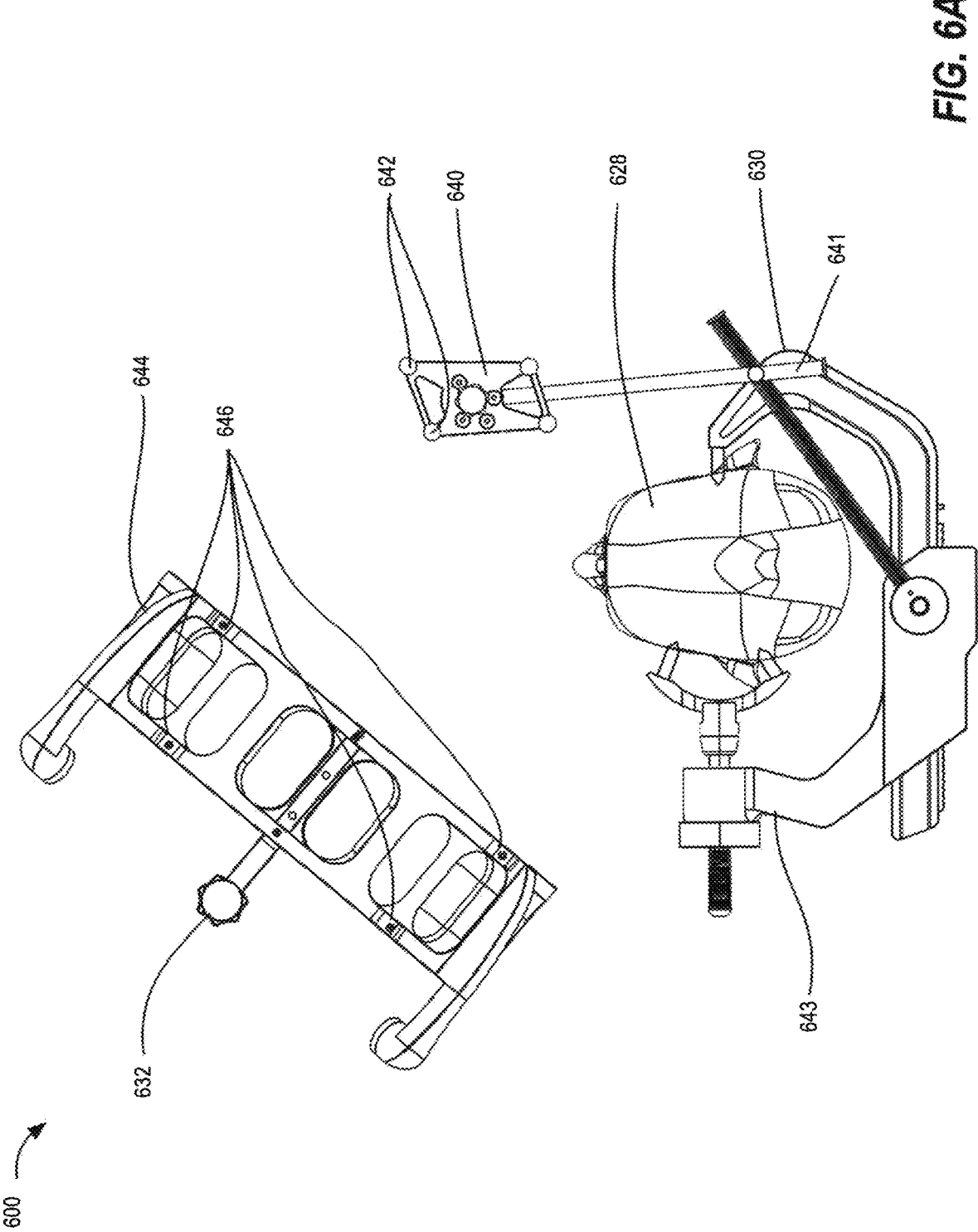
FIGS. 6A and 6B illustrate a system for registering an anatomical feature of a patient using fluoroscopy (fluoro) imaging, according to some embodiments.
Figure 6B:
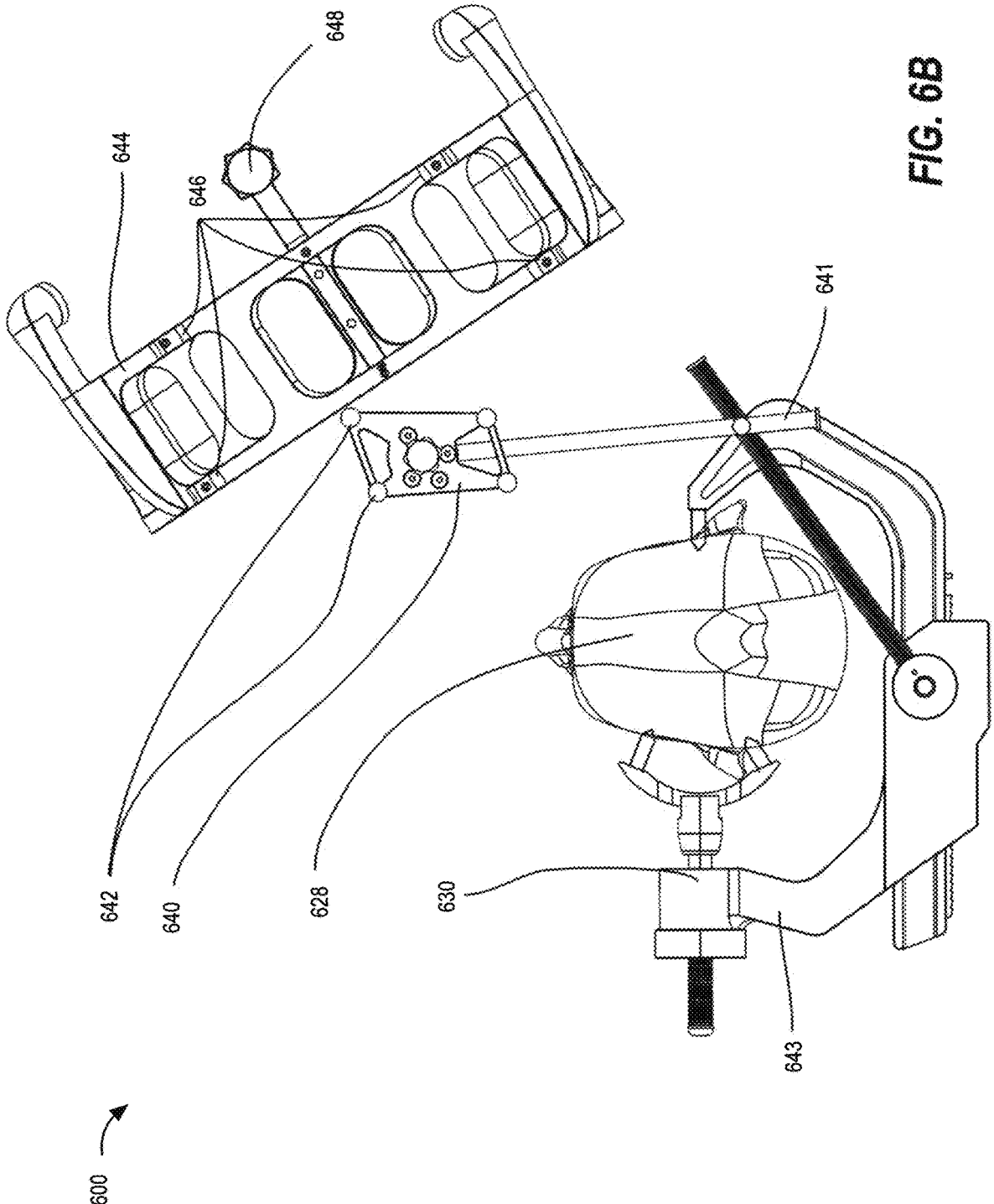

FIGS. 6A and 6B illustrate a system 600 for registering an anatomical feature of a patient using fluoroscopy (fluoro) imaging, according to some embodiments. In this embodiment, image space is registered to tracking space using multiple intraoperative fluoroscopy (fluoro) images taken using a tracked registration fixture 644. The anatomical feature of the patient (e.g., the patient's head 628) is positioned and rigidly affixed in a clamping apparatus 643 in a static position for the remainder of the procedure. The clamping apparatus 643 for rigid patient fixation can be a three-pin fixation system such as a Mayfield clamp, a stereotactic frame base attached to the surgical table, or another fixation method, as desired. The clamping apparatus 643 may also function as a support structure for a patient tracking array or DRB 640 as well. The DRB may be attached to the clamping apparatus using auxiliary mounting arms 641 or other means.

Once the patient is positioned, the fluoro fixture 644 is attached the fluoro unit's x-ray collecting image intensifier (not shown) and secured by tightening clamping feet 632. The fluoro fixture 644 contains fiducial markers (e.g., metal spheres laid out across two planes in this example, not shown) that are visible on 2D fluoro images captured by the fluoro image capture device and can be used to calculate the location of the x-ray source relative to the image intensifier, which is typically about 1 meter away contralateral to the patient, using a standard pinhole camera model. Detection of the metal spheres in the fluoro image captured by the fluoro image capture device also enables the software to de-warp the fluoro image (i.e., to remove pincushion and s-distortion). Additionally, the fluoro fixture 644 contains 3 or more tracking markers 646 for determining the location and orientation of the fluoro fixture 644 in tracking space. In some embodiments, software can project vectors through a CT image volume, based on a previously captured CT image, to generate synthetic images based on contrast levels in the CT image that appear similar to the actual fluoro images (i.e., digitally reconstructed radiographs (DRRs)). By iterating through theoretical positions of the fluoro beam until the DRRs match the actual fluoro shots, a match can be found between fluoro image and DRR in two or more perspectives, and based on this match, the location of the patient's head 628 relative to the x-ray source and detector is calculated. Because the tracking markers 646 on the fluoro fixture 644 track the position of the image intensifier and the position of the x-ray source relative to the image intensifier is calculated from metal fiducials on the fluoro fixture 644 projected on 2D images, the position of the x-ray source and detector in tracking space are known and the system is able to achieve image-to-tracking registration.

As shown by FIGS. 6A and 6B, two or more shots are taken of the head 628 of the patient by the fluoro image capture device from two different perspectives while tracking the array markers 642 of the DRB 640, which is fixed to the registration fixture 630 via a mounting arm 641, and tracking markers 646 on the fluoro fixture 644. Based on the tracking data and fluoro data, an algorithm computes the location of the head 628 or other anatomical feature relative to the tracking space for the procedure. Through image-to-tracking registration, the location of any tracked tool in the image volume space can be calculated.

For example, in one embodiment, a first fluoro image taken from a first fluoro perspective can be compared to a first DRR constructed from a first perspective through a CT image volume, and a second fluoro image taken from a second fluoro perspective can be compared to a second DRR constructed from a second perspective through the same CT image volume. Based on the comparisons, it may be determined that the first DRR is substantially equivalent to the first fluoro image with respect to the projected view of the anatomical feature, and that the second DRR is substantially equivalent to the second fluoro image with respect to the projected view of the anatomical feature. Equivalency confirms that the position and orientation of the x-ray path from emitter to collector on the actual fluoro machine as tracked in camera space matches the position and orientation of the x-ray path from emitter to collector as specified when generating the DRRs in CT space, and therefore registration of tracking space to CT space is achieved.

Figure 7:
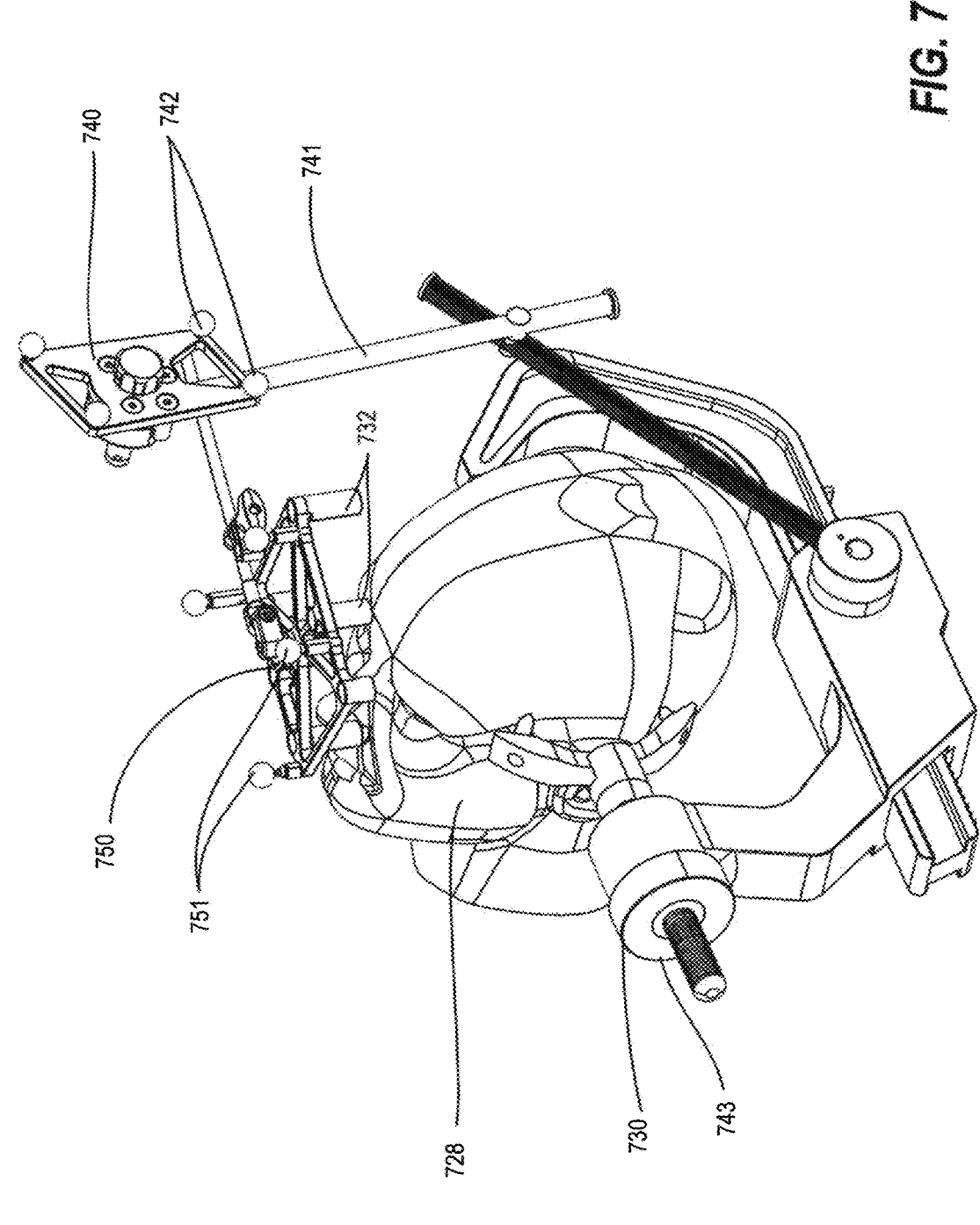
FIG. 7 illustrates a system for registering an anatomical feature of a patient using an intraoperative CT fixture (ICT) and a DRB, according to some embodiments.

FIG. 7 illustrates a system 700 for registering an anatomical feature of a patient using an intraoperative CT fixture (ICT) and a DRB, according to some embodiments. As shown in FIG. 7, in one application, a fiducial-based image-to-tracking registration can be utilized that uses an intraoperative CT fixture (ICT) 750 having a plurality of tracking markers 751 and radio-opaque fiducial reference markers 732 to register the CT space to the tracking space. After stabilizing the anatomical feature 728 (e.g., the patient's head) using clamping apparatus 730 such as a three-pin Mayfield frame and/or stereotactic frame, the surgeon will affix the ICT 750 to the anatomical feature 728, DRB 740, or clamping apparatus 730, so that it is in a static position relative to the tracking markers 742 of the DRB 740, which may be held in place by mounting arm 741 or other rigid means. A CT scan is captured that encompasses the fiducial reference markers 732 of the ICT 750 while also capturing relevant anatomy of the anatomical feature 728. Once the CT scan is loaded in the software, the system auto-identifies (through image processing) locations of the fiducial reference markers 732 of the ICT within the CT volume, which are in a fixed position relative to the tracking markers of the ICT 750, providing image-to-tracking registration. This registration, which was initially based on the tracking markers 751 of the ICT 750, is then related to or transferred to the tracking markers 742 of the DRB 740, and the ICT 750 may then be removed.

Figure 8A:
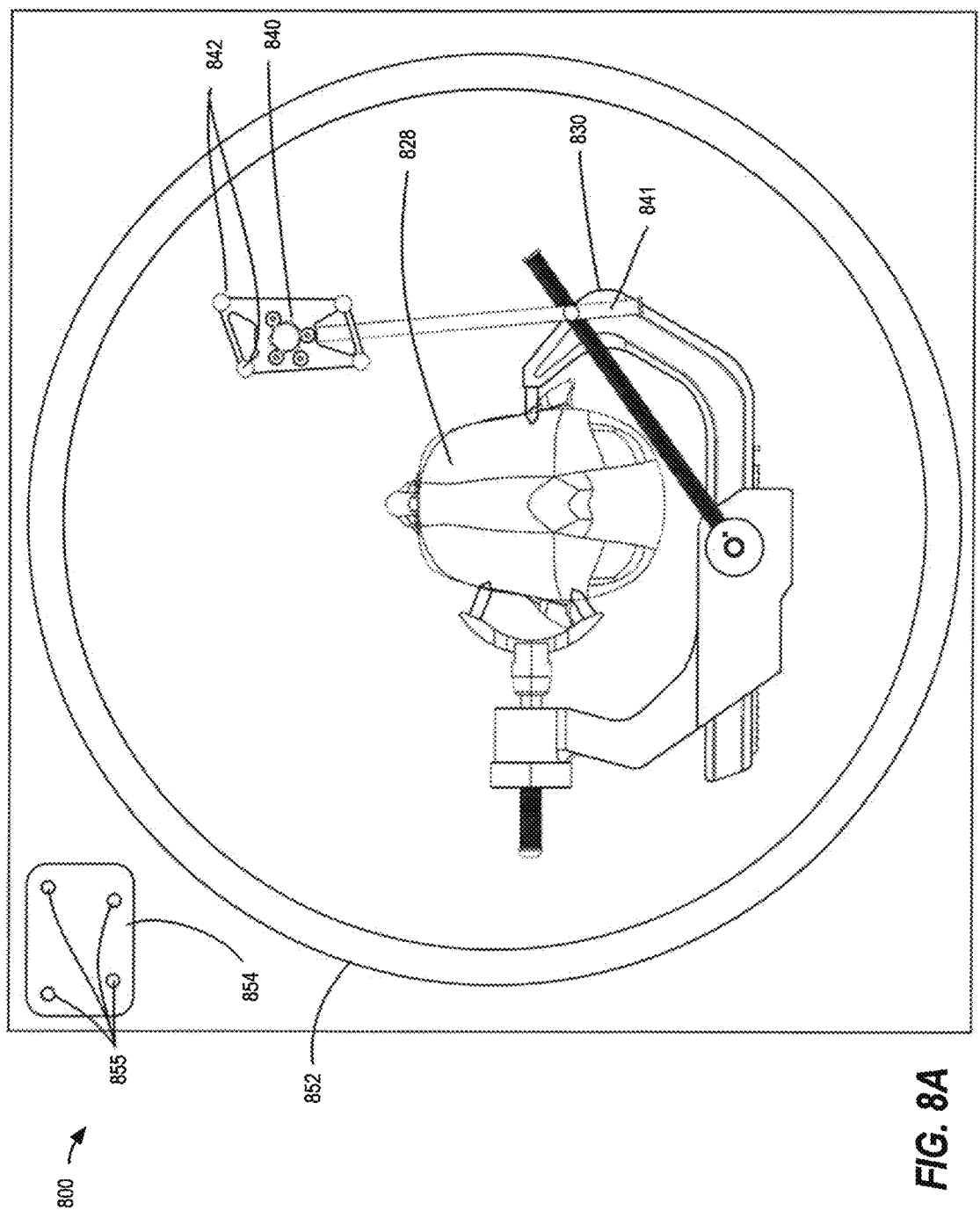
FIGS. 8A and 8B illustrate systems for registering an anatomical feature of a patient using a DRB and an X-ray cone beam imaging device, according to some embodiments.

FIG. 8A illustrates a system 800 for registering an anatomical feature of a patient using a DRB and an X-ray cone beam imaging device, according to some embodiments. An intraoperative scanner 852, such as an X-ray machine or other scanning device, may have a tracking array 854 with tracking markers 855, mounted thereon for registration. Based on the fixed, known position of the tracking array 854 on the scanning device, the system may be calibrated to directly map (register) the tracking space to the image space of any scan acquired by the system. Once registration is achieved, the registration, which is initially based on the tracking markers 855 (e.g. gantry markers) of the scanner's array 854, is related or transferred to the tracking markers 842 of a DRB 840, which may be fixed to a clamping fixture 830 holding the patient's head 828 by a mounting arm 841 or other rigid means. After transferring registration, the markers on the scanner are no longer used and can be removed, deactivated or covered if desired. Registering the tracking space to any image acquired by a scanner in this way may avoid the need for fiducials or other reference markers in the image space in some embodiments.

Figure 8B:
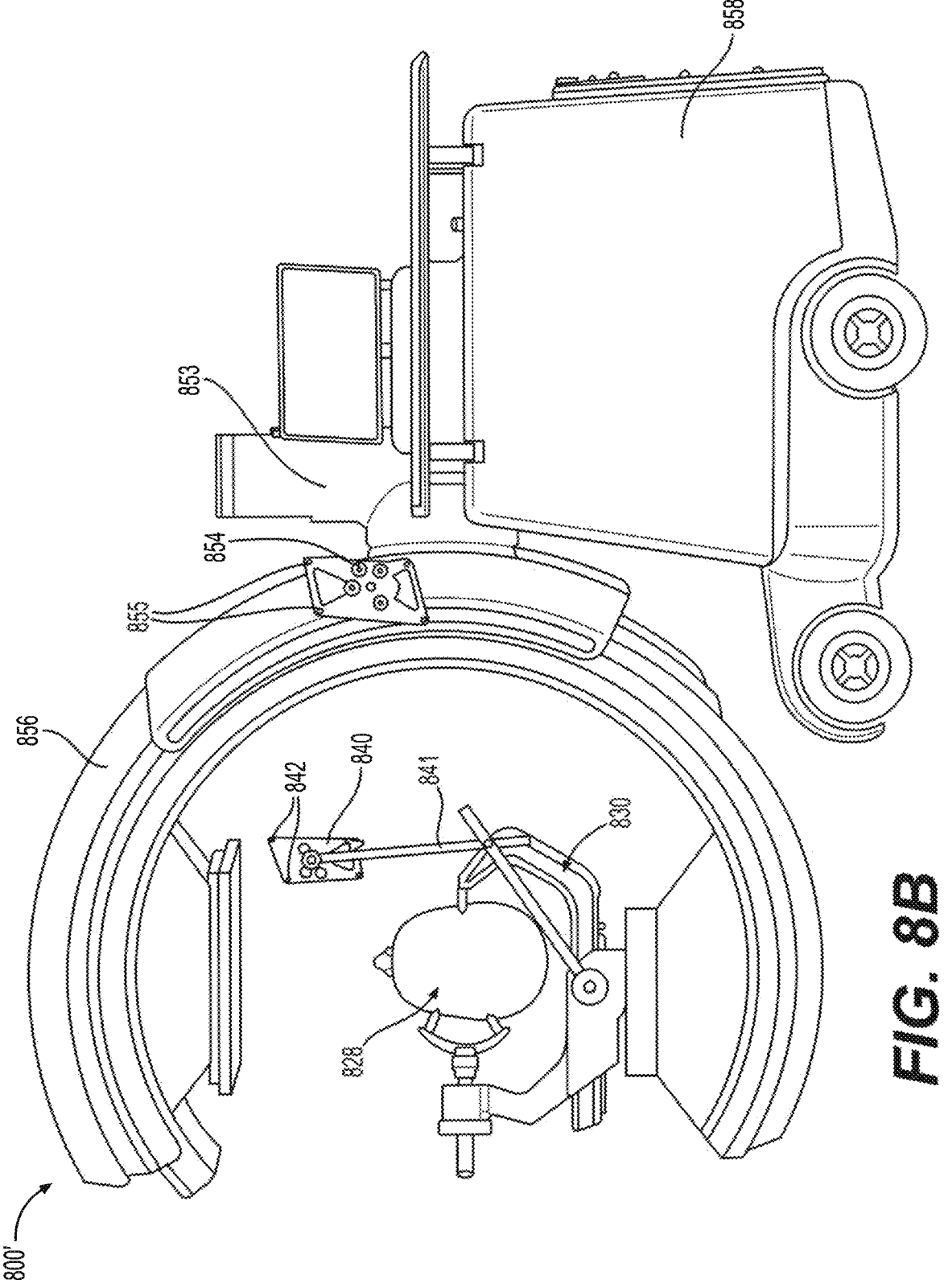

FIG. 8B illustrates an alternative system 800' that uses a portable intraoperative scanner, referred to herein as a C-arm scanner 853. In this example, the C-arm scanner 853 includes a c-shaped arm 856 coupled to a movable base 858 to allow the C-arm scanner 853 to be moved into place and removed as needed, without interfering with other aspects of the surgery. The arm 856 is positioned around the patient's head 828 intraoperatively, and the arm 856 is rotated and/or translated with respect to the patient's head 828 to capture the X-ray or other type of scan that to achieve registration, at which point the C-arm scanner 853 may be removed from the patient.

Another registration method for an anatomical feature of a patient, e.g., a patient's head, may be to use a surface contour map of the anatomical feature, according to some embodiments. A surface contour map may be constructed using a navigated or tracked probe, or other measuring or sensing device, such as a laser pointer, 3D camera, etc. For example, a surgeon may drag or sequentially touch points on the surface of the head with the navigated probe to capture the surface across unique protrusions, such as zygomatic bones, superciliary arches, bridge of nose, eyebrows, etc. The system then compares the resulting surface contours to contours detected from the CT and/or MR images, seeking the location and orientation of contour that provides the closest match. To account for movement of the patient and to ensure that all contour points are taken relative to the same anatomical feature, each contour point is related to tracking markers on a DRB on the patient at the time it is recorded. Since the location of the contour map is known in tracking space from the tracked probe and tracked DRB, tracking-to-image registration is obtained once the corresponding contour is found in image space.

Figure 9:
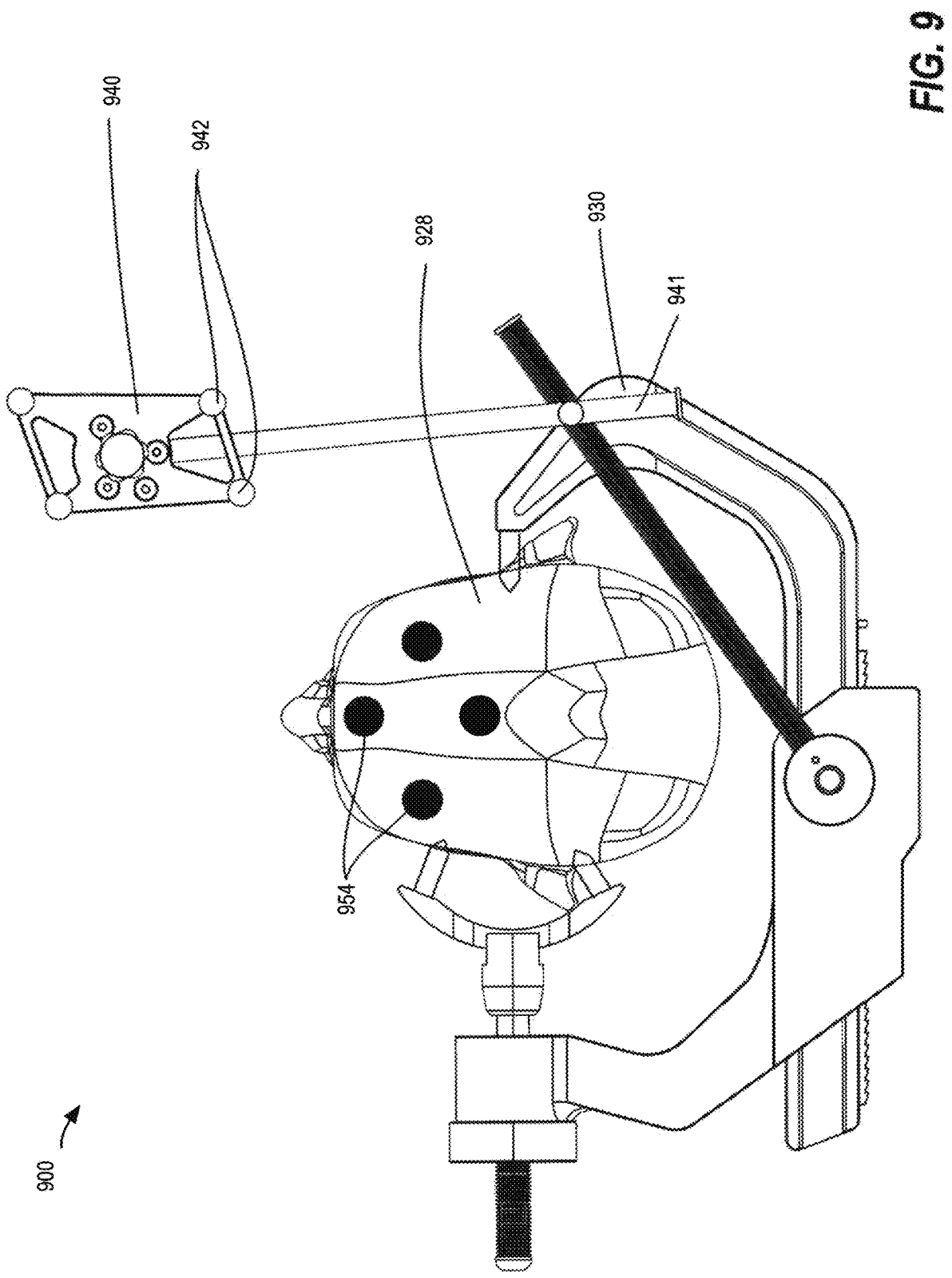
FIG. 9 illustrates a system for registering an anatomical feature of a patient using a navigated probe and fiducials for point-to-point mapping of the anatomical feature, according to some embodiments.

FIG. 9 illustrates a system 900 for registering an anatomical feature of a patient using a navigated or tracked probe and fiducials for point-to-point mapping of the anatomical feature 928 (e.g., a patient's head), according to some embodiments. Software would instruct the user to point with a tracked probe to a series of anatomical landmark points that can be found in the CT or MR image. When the user points to the landmark indicated by software, the system captures a frame of tracking data with the tracked locations of tracking markers on the probe and on the DRB. From the tracked locations of markers on the probe, the coordinates of the tip of the probe are calculated and related to the locations of markers on the DRB. Once 3 or more points are found in both spaces, tracking-to-image registration is achieved. As an alternative to pointing to natural anatomical landmarks, fiducials 954 (i.e., fiducial markers), such as sticker fiducials or metal fiducials, may be used. The surgeon will attach the fiducials 954 to the patient, which are constructed of material that is opaque on imaging, for example containing metal if used with CT or Vitamin E if used with MR. Imaging (CT or MR) will occur after placing the fiducials 954. The surgeon or user will then manually find the coordinates of the fiducials in the image volume, or the software will find them automatically with image processing. After attaching a DRB 940 with tracking markers 942 to the patient through a mounting arm 941 connected to a clamping apparatus 930 or other rigid means, the surgeon or user may also locate the fiducials 954 in physical space relative to the DRB 940 by touching the fiducials 954 with a tracked probe while simultaneously recording tracking markers on the probe (not shown) and on the DRB 940. Registration is achieved because the coordinates of the same points are known in the image space and the tracking space.

One use for the embodiments described herein is to plan trajectories and to control a robot to move into a desired trajectory, after which the surgeon will place implants such as electrodes through a guide tube held by the robot. Additional functionalities include exporting coordinates used with existing stereotactic frames, such as a Leksell frame, which uses five coordinates: X, Y, Z, Ring Angle and Arc Angle. These five coordinates are established using the target and trajectory identified in the planning stage relative to the image space and knowing the position and orientation of the ring and arc relative to the stereotactic frame base or other registration fixture.

Figure 10:
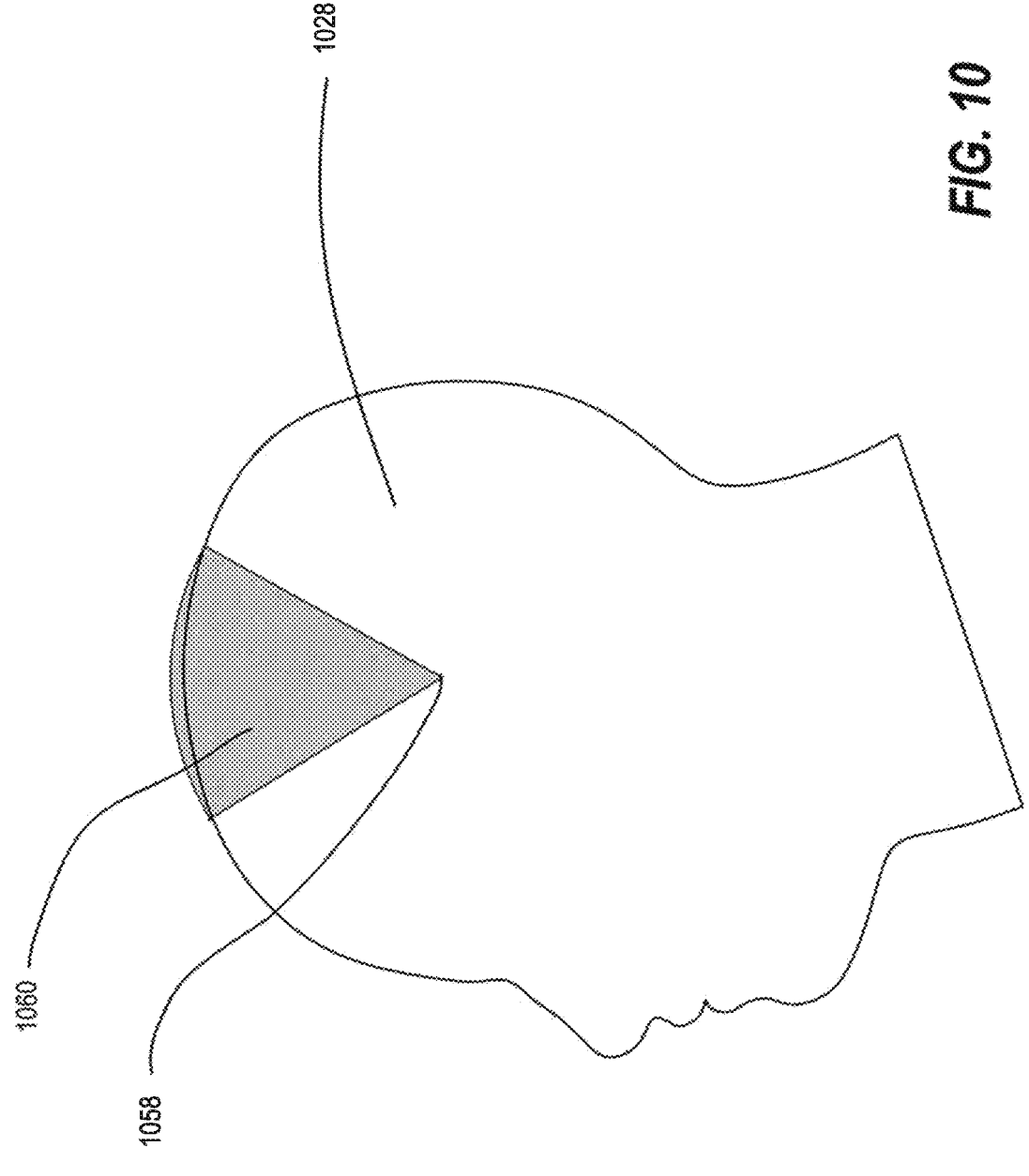
FIG. 10 illustrates a two-dimensional visualization of an adjustment range for a centerpoint-arc mechanism, according to some embodiments.

As shown in FIG. 10, stereotactic frames allow a target location 1058 of an anatomical feature 1028 (e.g., a patient's head) to be treated as the center of a sphere and the trajectory can pivot about the target location 1058. The trajectory to the target location 1058 is adjusted by the ring and arc angles of the stereotactic frame (e.g., a Leksell frame). These coordinates may be set manually, and the stereotactic frame may be used as a backup or as a redundant system in case the robot fails or cannot be tracked or registered successfully. The linear x,y,z offsets to the center point (i.e., target location 1058) are adjusted via the mechanisms of the frame. A cone 1060 is centered around the target location 1058, and shows the adjustment zone that can be achieved by modifying the ring and arc angles of the Leksell or other type of frame. This figure illustrates that a stereotactic frame with ring and arc adjustments is well suited for reaching a fixed target location from a range of angles while changing the entry point into the skull.

Figure 11:
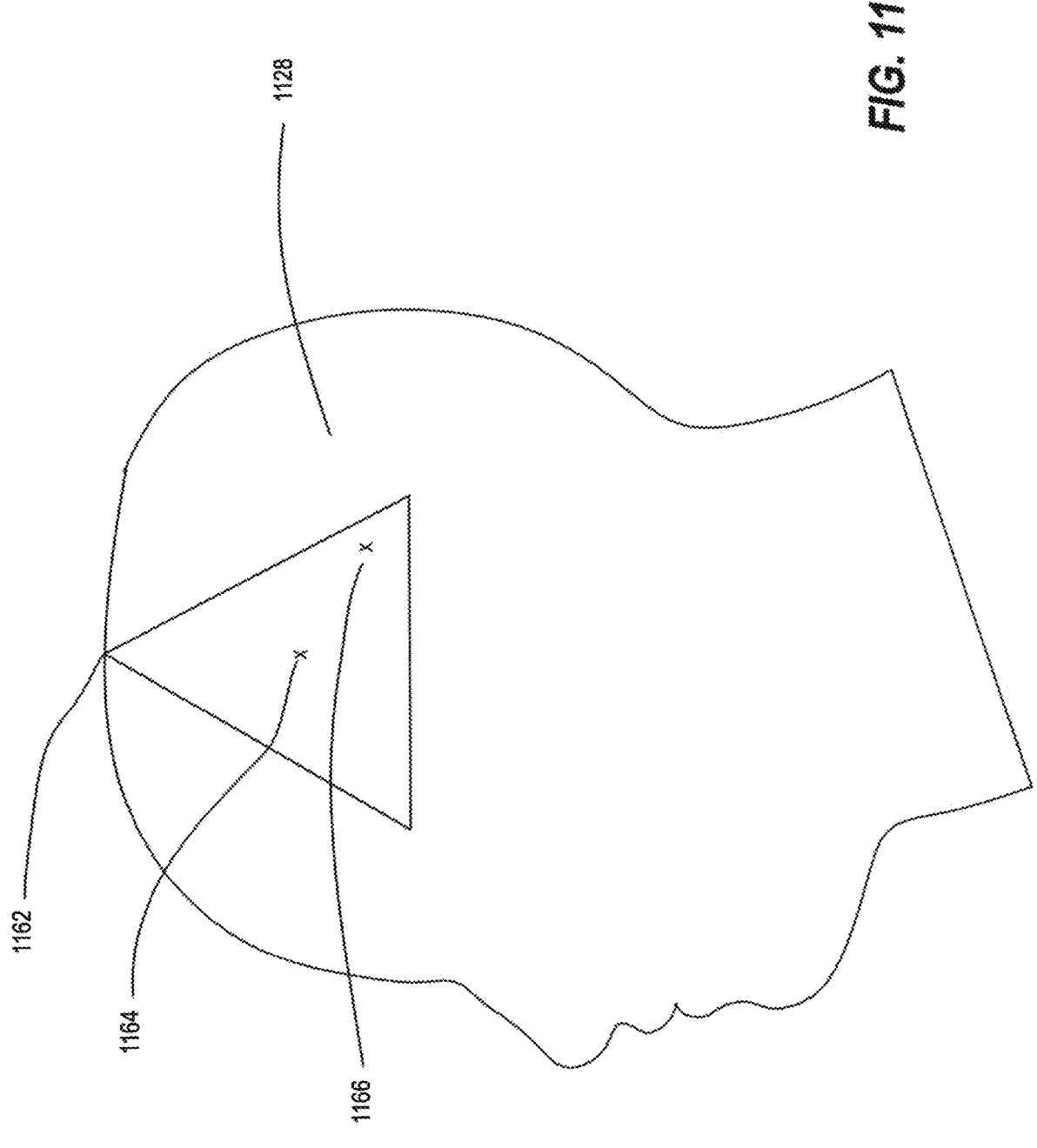
FIG. 11 illustrates a two-dimensional visualization of virtual point rotation mechanism, according to some embodiments.

FIG. 11 illustrates a two-dimensional visualization of virtual point rotation mechanism, according to some embodiments. In this embodiment, the robotic arm is able to create a different type of point-rotation functionality that enables a new movement mode that is not easily achievable with a 5-axis mechanical frame, but that may be achieved using the embodiments described herein. Through coordinated control of the robot's axes using the registration techniques described herein, this mode allows the user to pivot the robot's guide tube about any fixed point in space. For example, the robot may pivot about the entry point 1162 into the anatomical feature 1128 (e.g., a patient's head). This entry point pivoting is advantageous as it allows the user to make a smaller burr hole without limiting their ability to adjust the target location 1164 intraoperatively. The cone 1160 represents the range of trajectories that may be reachable through a single entry hole. Additionally, entry point pivoting is advantageous as it allows the user to reach two different target locations 1164 and 1166 through the same small entry burr hole. Alternately, the robot may pivot about a target point (e.g., location 1058 shown in FIG. 10) within the skull to reach the target location from different angles or trajectories, as illustrated in FIG. 10. Such interior pivoting robotically has the same advantages as a stereotactic frame as it allows the user to approach the same target location 1058 from multiple approaches, such as when irradiating a tumor or when adjusting a path so that critical structures such as blood vessels or nerves will not be crossed when reaching targets beyond them. Unlike a stereotactic frame, which relies on fixed ring and arc articulations to keep a target/pivot point fixed, the robot adjusts the pivot point through controlled activation of axes and the robot can therefore dynamically adjust its pivot point and switch as needed between the modes illustrated in FIGS. 10 and 11.

Following the insertion of implants or instrumentation using the robot or ring and arc fixture, these and other embodiments may allow for implant locations to be verified using intraoperative imaging. Placement accuracy of the instrument or implant relative to the planned trajectory can be qualitatively and/or quantitatively shown to the user. One option for comparing planned to placed position is to merge a postoperative verification CT image to any of the preoperative images. Once pre- and post-operative images are merged and plan is shown overlaid, the shadow of the implant on postop CT can be compared to the plan to assess accuracy of placement. Detection of the shadow artifact on post-op CT can be performed automatically through image processing and the offset displayed numerically in terms of millimeters offset at the tip and entry and angular offset along the path. This option does not require any fiducials to be present in the verification image since image-to-image registration is performed based on bony anatomical contours.

A second option for comparing planned position to the final placement would utilize intraoperative fluoro with or without an attached fluoro fixture. Two out-of-plane fluoro images will be taken and these fluoro images will be matched to DRRs generated from pre-operative CT or MR as described above for registration. Unlike some of the registration methods described above, however, it may be less important for the fluoro images to be tracked because the key information is where the electrode is located relative to the anatomy in the fluoro image. The linear or slightly curved shadow of the electrode would be found on a fluoro image, and once the DRR corresponding to that fluoro shot is found, this shadow can be replicated in the CT image volume as a plane or sheet that is oriented in and out of the ray direction of the fluoro image and DRR. That is, the system may not know how deep in or out of the fluoro image plane the electrode lies on a given shot, but can calculate the plane or sheet of possible locations and represent this plane or sheet on the 3D volume. In a second fluoro view, a different plane or sheet can be determined and overlaid on the 3D image. Where these two planes or sheets intersect on the 3D image is the detected path of the electrode. The system can represent this detected path as a graphic on the 3D image volume and allow the user to reslice the image volume to display this path and the planned path from whatever perspective is desired, also allowing automatic or manual calculation of the deviation from planned to placed position of the electrode. Tracking the fluoro fixture is unnecessary but may be done to help de-warp the fluoro images and calculate the location of the x-ray emitter to improve accuracy of DRR calculation, the rate of convergence when iterating to find matching DRR and fluoro shots, and placement of sheets/planes representing the electrode on the 3D scan.

In this and other examples, it is desirable to maintain navigation integrity, i.e., to ensure that the registration and tracking remain accurate throughout the procedure. Two primary methods to establish and maintain navigation integrity include: tracking the position of a surveillance marker relative to the markers on the DRB, and checking landmarks within the images. In the first method, should this position change due to, for example, the DRB being bumped, then the system may alert the user of a possible loss of navigation integrity. In the second method, if a landmark check shows that the anatomy represented in the displayed slices on screen does not match the anatomy at which the tip of the probe points, then the surgeon will also become aware that there is a loss of navigation integrity. In either method, if using the registration method of CT localizer and frame reference array (FRA), the surgeon has the option to reattach the FRA, which mounts in only one possible way to the frame base, and to restore tracking-to-image registration based on the FRA tracking markers and the stored fiducials from the CT localizer 536. This registration can then be transferred or related to tracking markers on a repositioned DRB. Once registration is transferred the FRA can be removed if desired.

Referring now to FIGS. 12-18 generally, with reference to the surgical robot system 100 shown in FIG. 1A, end-effector 112 may be equipped with components, configured, or otherwise include features so that one end-effector may remain attached to a given one of robot arms 104 without changing to another end-effector for multiple different surgical procedures, such as, by way of example only, Deep Brain Stimulation (DBS), Stereoelectroencephalography (SEEG), or Endoscopic Navigation and Tumor Biopsy. As discussed previously, end-effector 112 may be orientable to oppose an anatomical feature of a patient in the manner so as to be in operative proximity thereto, and, to be able to receive one or more surgical tools for operations contemplated on the anatomical feature proximate to the end-effector 112. Motion and orientation of end-effector 112 may be accomplished through any of the navigation, trajectory guidance, or other methodologies discussed herein or as may be otherwise suitable for the particular operation.

End-effector 112 is suitably configured to permit a plurality of surgical tools 129 to be selectively connectable to end-effector 112. Thus, for example, a stylet 113 (FIG. 13) may be selectively attached in order to localize an incision point on an anatomical feature of a patient, or an electrode driver 115 (FIG. 14) may be selectively attached to the same end-effector 112.

With reference to the previous discussion of robot surgical system 100, a processor circuit, as well as memory accessible by such processor circuit, includes various subroutines and other machine-readable instructions configured to cause, when executed, end-effector 112 to move, such as by GPS movement, relative to the anatomical feature, at predetermined stages of associated surgical operations, whether pre-operative, intra-operative or post-operative.

Figure 12:
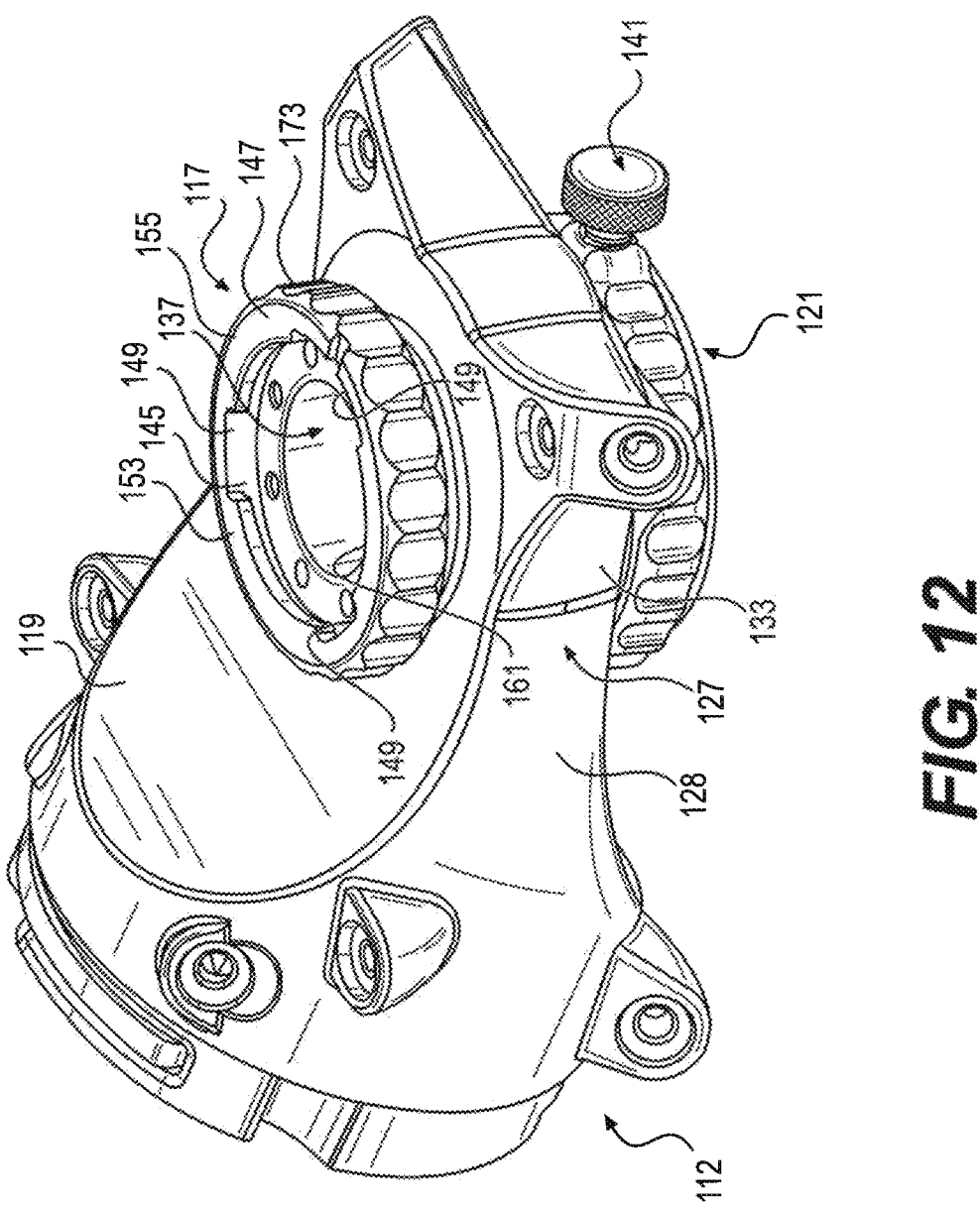
FIG. 12 is an isometric view of one possible implementation of an end-effector according to the present disclosure.

End-effector 112 includes various components and features to either prevent or permit end-effector movement depending on whether and which tools 129, if any, are connected to end-effector 112. Referring more particularly to FIG. 12, end-effector 112 includes a tool-insert locking mechanism 117 located on and connected to proximal surface 119. Tool-insert locking mechanism 117 is configured so as to secure any selected one of a plurality of surgical tools, such as the aforesaid stylet 113, electrode driver 115, or any other tools for different surgeries mentioned previously or as may be contemplated by other applications of this disclosure. The securement of the tool by tool-insert locking mechanism 117 is such that, for any of multiple tools capable of being secured to locking mechanism 117, each such tool is operatively and suitably secured at the predetermined height, angle of orientation, and rotational position relative to the anatomical feature of the patient, such that multiple tools may be secured to the same end-effector 112 in respective positions appropriate for the contemplated procedure.

Another feature of the end-effector 112 is a tool stop 121 located on distal surface 123 of end-effector 112, that is, the surface generally opposing the patient. Tool stop 121 has a stop mechanism 125 and a sensor 127 operatively associated therewith, as seen with reference to FIGS. 16, 19, and 20. Stop mechanism 125 is mounted to end-effector 112 so as to be selectively movable relative thereto between an engaged position to prevent any of the tools from being connected to end-effector 112 and a disengaged position which permits any of the tools 129 to be selectively connected to end-effector 112. Sensor 127 may be located on or within the housing of end-effector 112 at any suitable location (FIGS. 12, 14, 16) so that sensor 127 detects whether stop mechanism 125 is in the engaged or disengaged position. Sensor 127 may assume any form suitable for such detection, such as any type of mechanical switch or any type of magnetic sensor, including Reed switches, Hall Effect sensors, or other magnetic field detecting devices. In one possible implementation, sensor 127 has two portions, a Hall Effect sensor portion (not shown) and a magnetic portion 131, the two portions moving relative to each other so as to generate and detect two magnetic fields corresponding to respective engaged and disengaged position. In the illustrated implementation, the magnetic portion comprises two rare earth magnets 131 which move relative to the complementary sensing portion (not shown) mounted in the housing of end effector 112 in operative proximity to magnets 131 to detect change in the associated magnetic field from movement of stop mechanism 125 between engaged and disengaged positions. In this implementation the Hall effect sensor is bipolar and can detect whether a North pole or South pole of a magnet opposes the sensor. Magnets 131 are configured so that the North pole of one magnet faces the path of the sensor and the South pole of the other magnet faces the path of the sensor. In this configuration, the sensor senses an increased signal when it is near one magnet (for example, in disengaged position), a decreased signal when it is near the other magnet (for example, in engaged position), and unchanged signal when it is not in proximity to any magnet. In this implementation, in response to detection of stop mechanism 125 being in the disengaged position shown in FIGS. 13 and 19, sensor 127 causes the processor of surgical robot system 100 to execute suitable instructions to prevent movement of end-effector 112 relative to the anatomical feature. Such movement prevention may be appropriate for any number of reasons, such as when a tool is connected to end-effector 112, such tool potentially interacting with the anatomical feature of the patient.

Another implementation of a sensor 127 for detecting engaged or disengaged tool stop mechanism 125 could comprise a single magnet behind the housing (not shown) and two Hall Effect sensors located where magnets 131 are shown in the preferred embodiment. In such a configuration, monopolar Hall Effect sensors are suitable and would be configured so that Sensor 1 detects a signal when the magnet is in proximity due to the locking mechanism being disengaged, while Sensor 2 detects a signal when the same magnet is in proximity due to the locking mechanism being engaged. Neither sensor would detect a signal when the magnet is between positions or out of proximity to either sensor. Although a configuration could be conceived in which a sensor is active for engaged position and inactive for disengaged position, a configuration with three signals indicating engaged, disengaged, or transitional is preferred to ensure correct behavior in case of power failure.

End-effector 112, tool stop 121, and tool-insert locking mechanism 117 each have co-axially aligned bores or apertures such that any selected one of the plurality of surgical tools 129 may be received through such bores and apertures. In this implementation end-effector has a bore 133 and tool stop 121 and tool-insert locking mechanism 117 have respective apertures 135 and 137. Stop mechanism 125 includes a ring 139 axially aligned with bore 133 and aperture 135 of tool stop 121. Ring 139 is selectively, manually rotatable in the directions indicated by arrow A (FIG. 16) so as to move stop mechanism 125 between the engaged position and the disengaged position.

In one possible implementation, the selective rotation of ring 139 includes features which enable ring 139 to be locked in either the disengaged or engaged position. So, for example, as illustrated, a detent mechanism 141 is located on and mounted to ring 139 in any suitable way to lock ring 139 against certain rotational movement out of a predetermined position, in this case, such position being when stop mechanism 125 is in the engaged position. Although various forms of detent mechanism are contemplated herein, one suitable arrangement has a manually accessible head extending circumferentially outwardly from ring 139 and having a male protrusion (not shown) spring-loaded axially inwardly to engage a corresponding female detent portion (not shown). Detent mechanism 141, as such, is manually actuatable to unlock ring 139 from its engaged position to permit ring 139 to be manually rotated to cause stop mechanism 125 to move from the engaged position (FIG. 20) to the disengaged position (FIG. 19).

Figure 16:
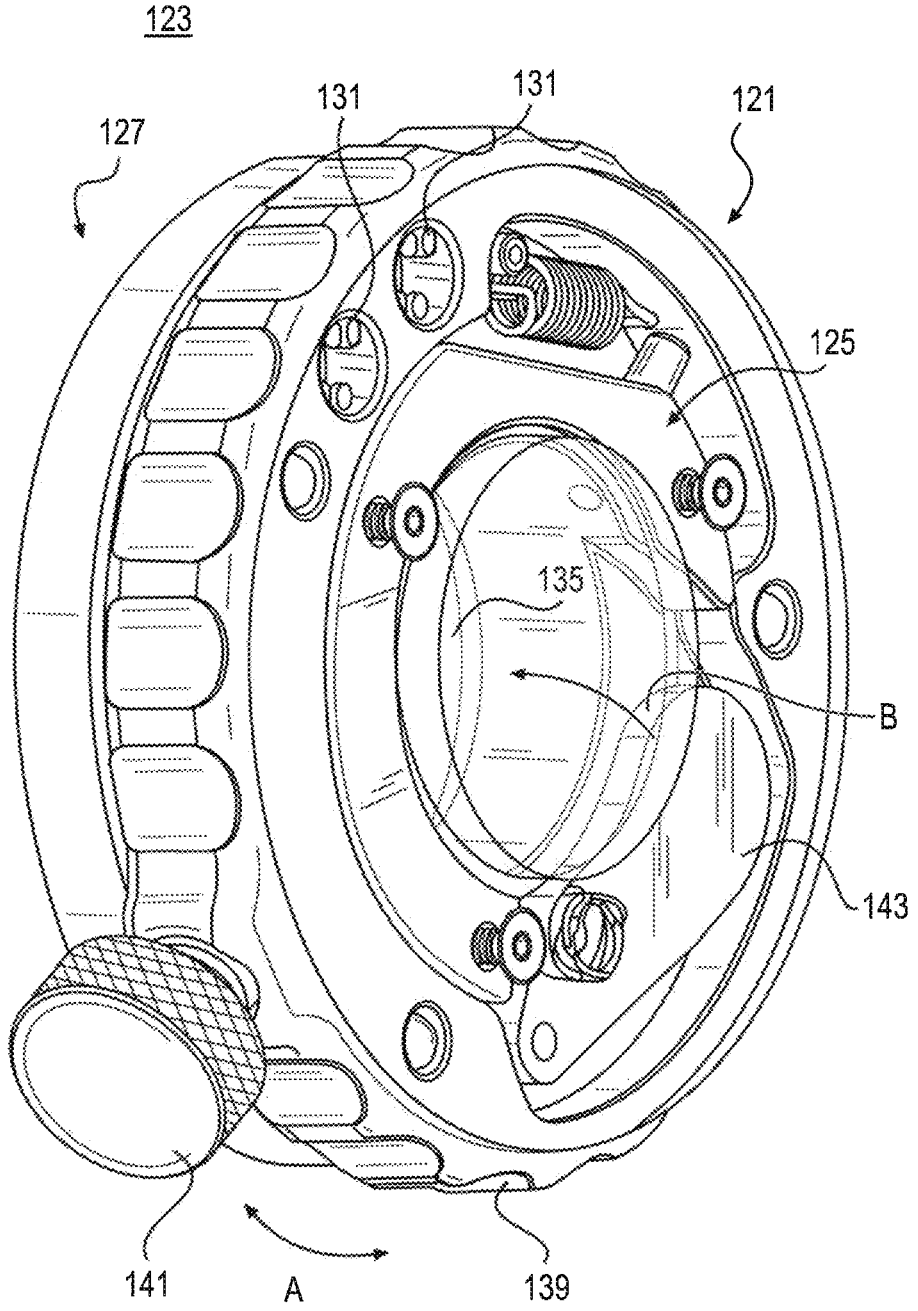
FIG. 16 is an isometric view of one possible tool stop for use with an end-effector according to the present disclosure.
Figure 19:
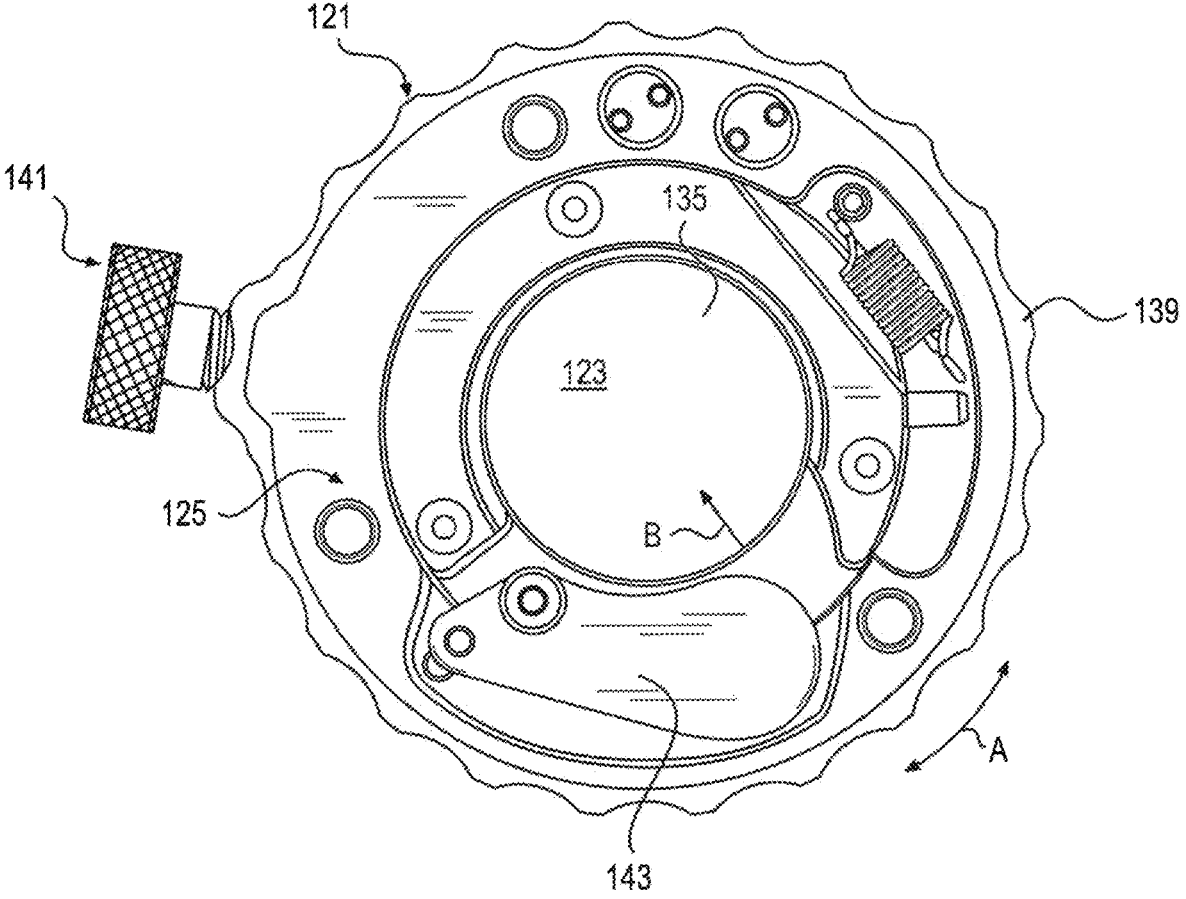
FIGS. 19 and 20 are top plan views of the tool stop of FIG. 16, showing open and closed positions, respectively.
Figure 20:
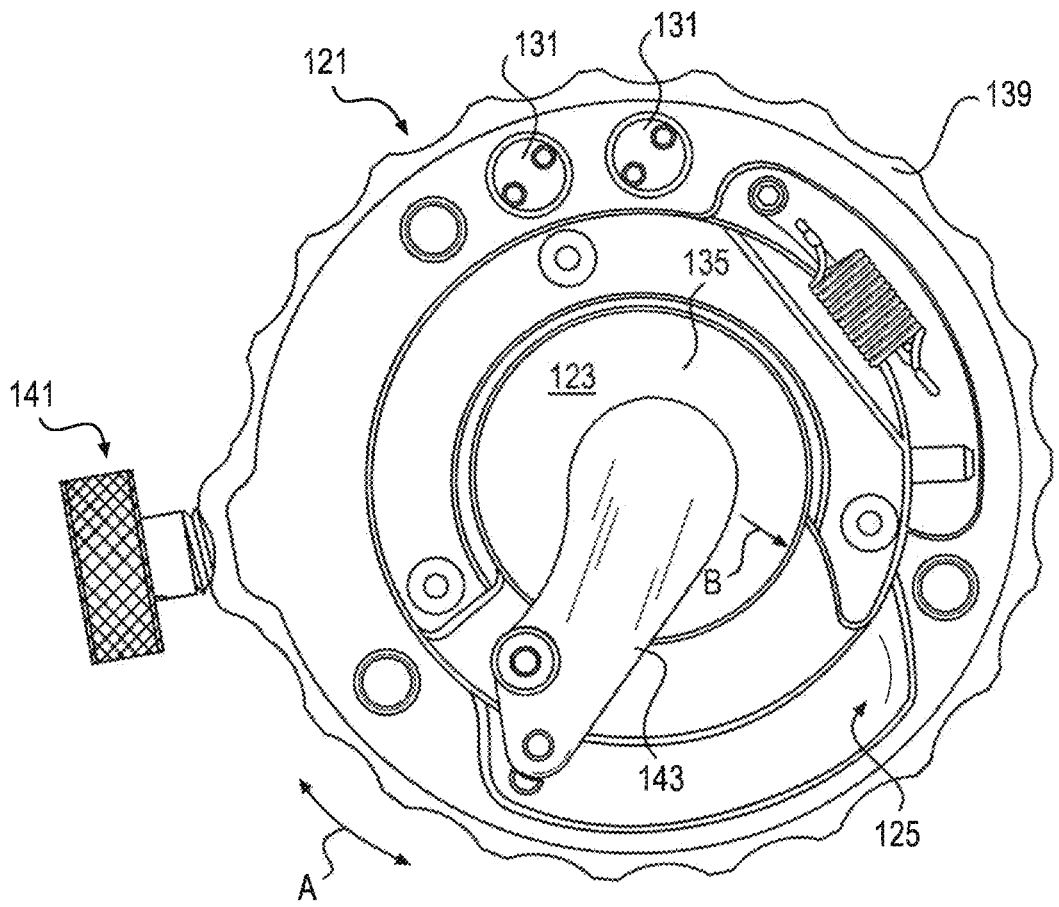
Figure 21:
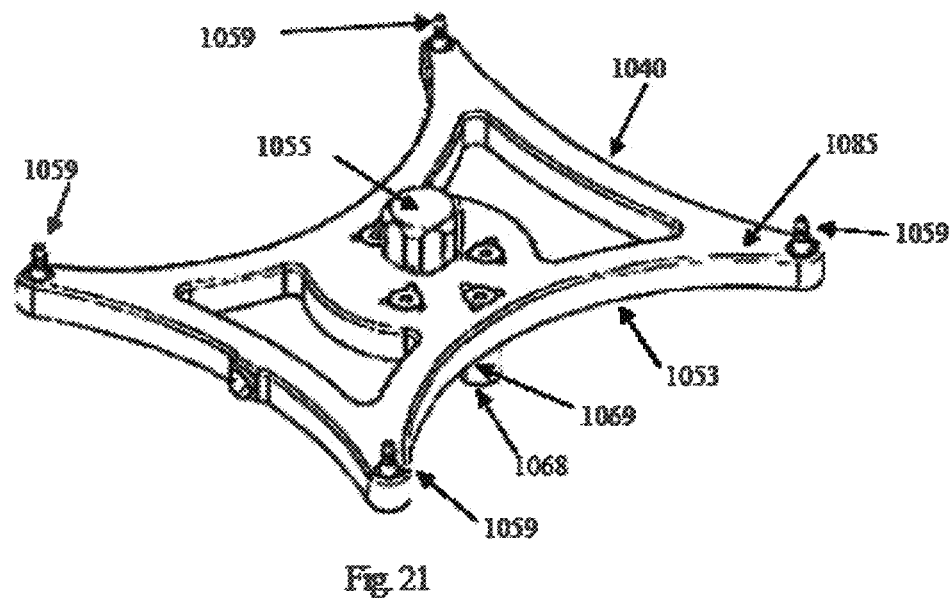
FIG. 21 is a first, isometric view of a detachable base in the form of a detachable dynamic reference base for use in the robot system disclosed herein and the associated registration systems.

Tool stop 121 includes a lever arm 143 pivotally mounted adjacent aperture 135 of tool stop 121 so end of lever arm 143 selectively pivots in the directions indicated by arrow B (FIGS. 16, 19 and 20). Lever arm 143 is operatively connected to stop mechanism 125, meaning it closes aperture 135 of tool stop 121 in response to stop mechanism 125 being in the engaged position, as shown in FIG. 20. Lever arm 143 is also operatively connected so as to pivot back in direction of arrow B to open aperture 135 in response to stop mechanism 125 being in the disengaged position. As such, movement of stop mechanism 125 between engaged and disengaged positions results in closure or opening of aperture 135, respectively, by lever arm 143.

Lever arm 143, in this implementation, is not only pivotally mounted adjacent aperture 135, but also pivots in parallel with a distal plane defined at a distal-most point of distal surface 123 of end-effector 112. In this manner, any one of the surgical tools 129, which is attempted to be inserted through bore 133 and aperture 135, is stopped from being inserted past the distal plane in which lever arm 143 rotates to close aperture 135.

Figure 13:
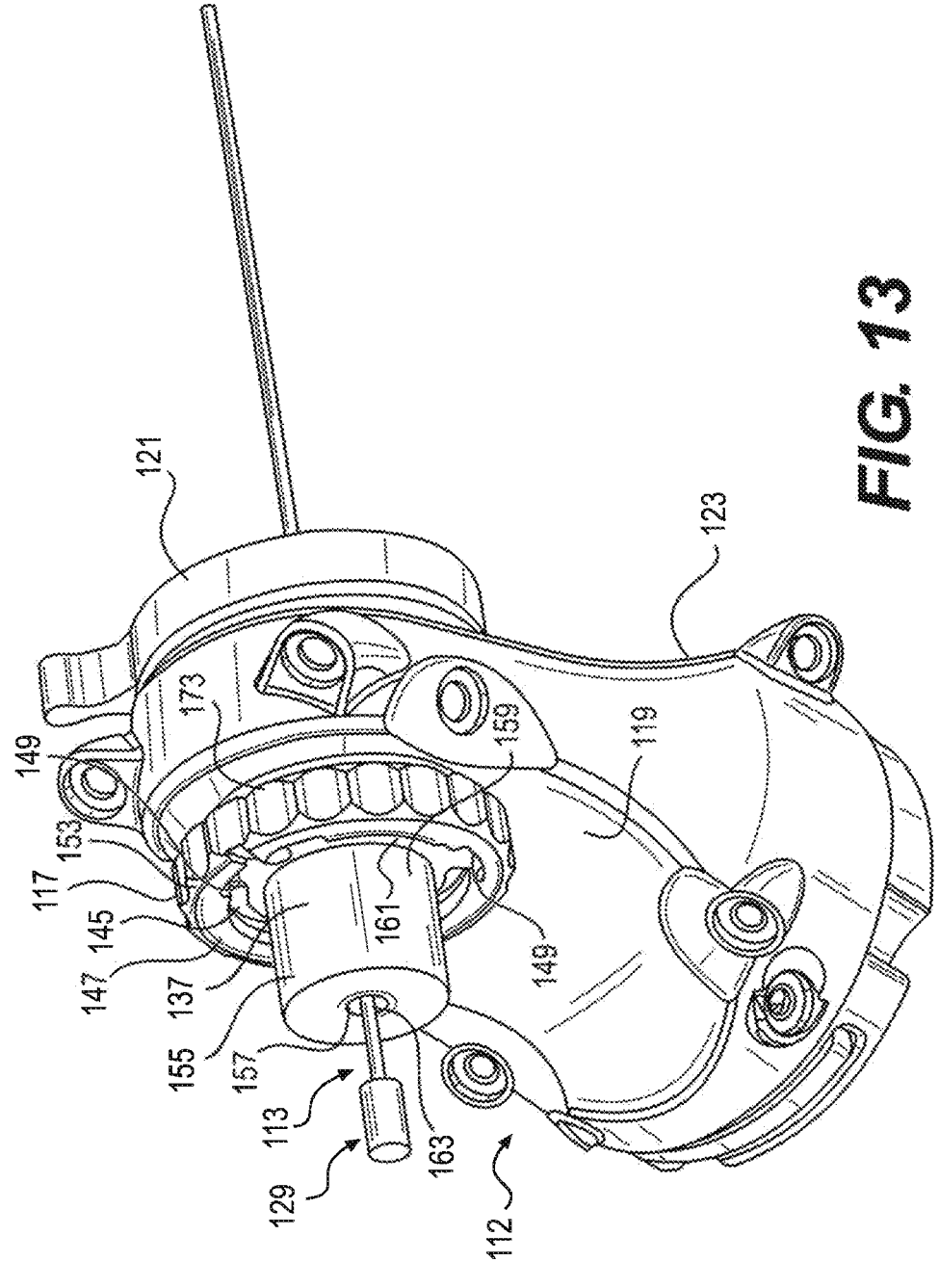
FIG. 13 is an isometric view of another possible implementation of an end-effector of the present disclosure.
Figure 14:
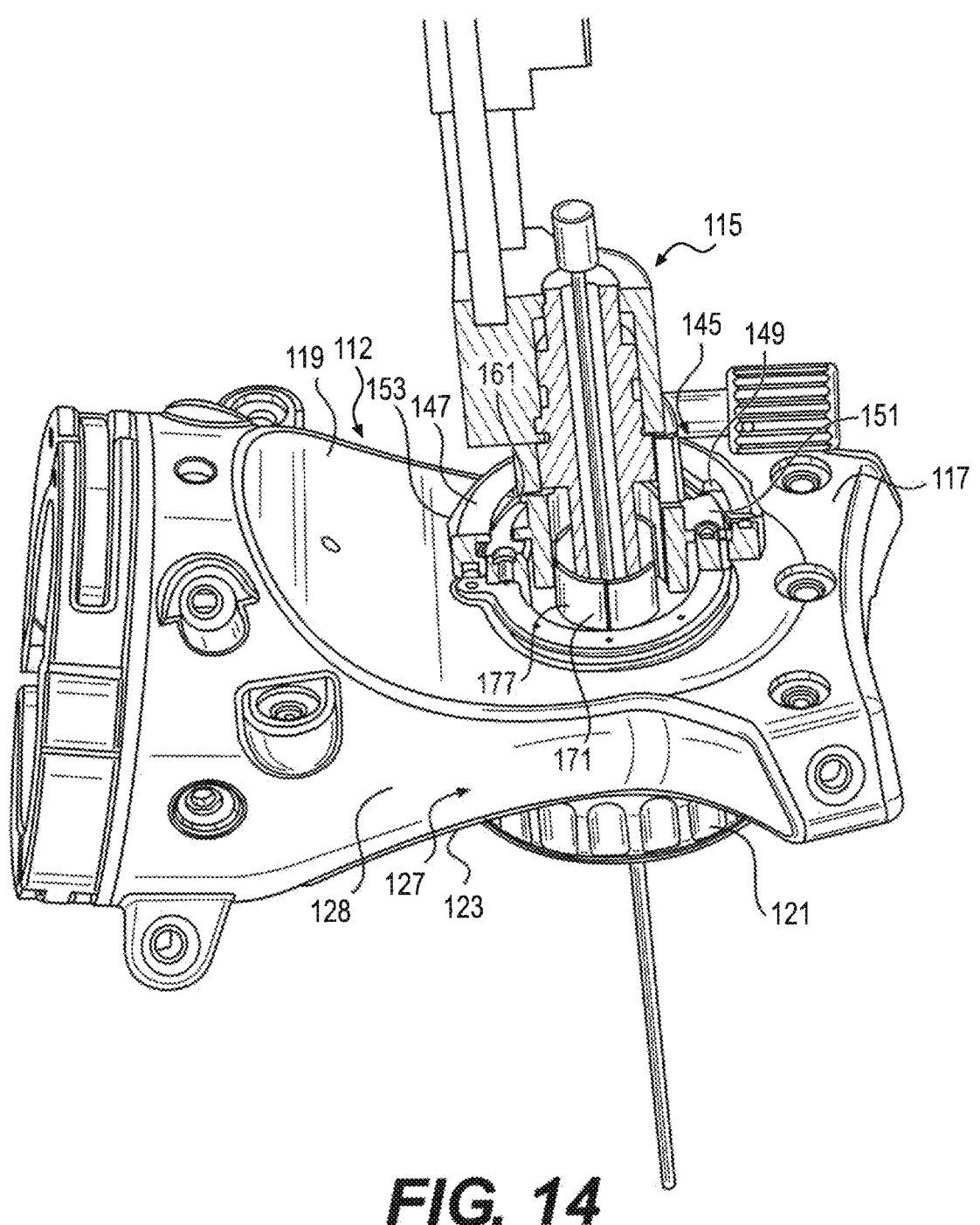
FIG. 14 is a partial cutaway, isometric view of still another possible implementation of an end-effector according to the present disclosure.
Figure 15:
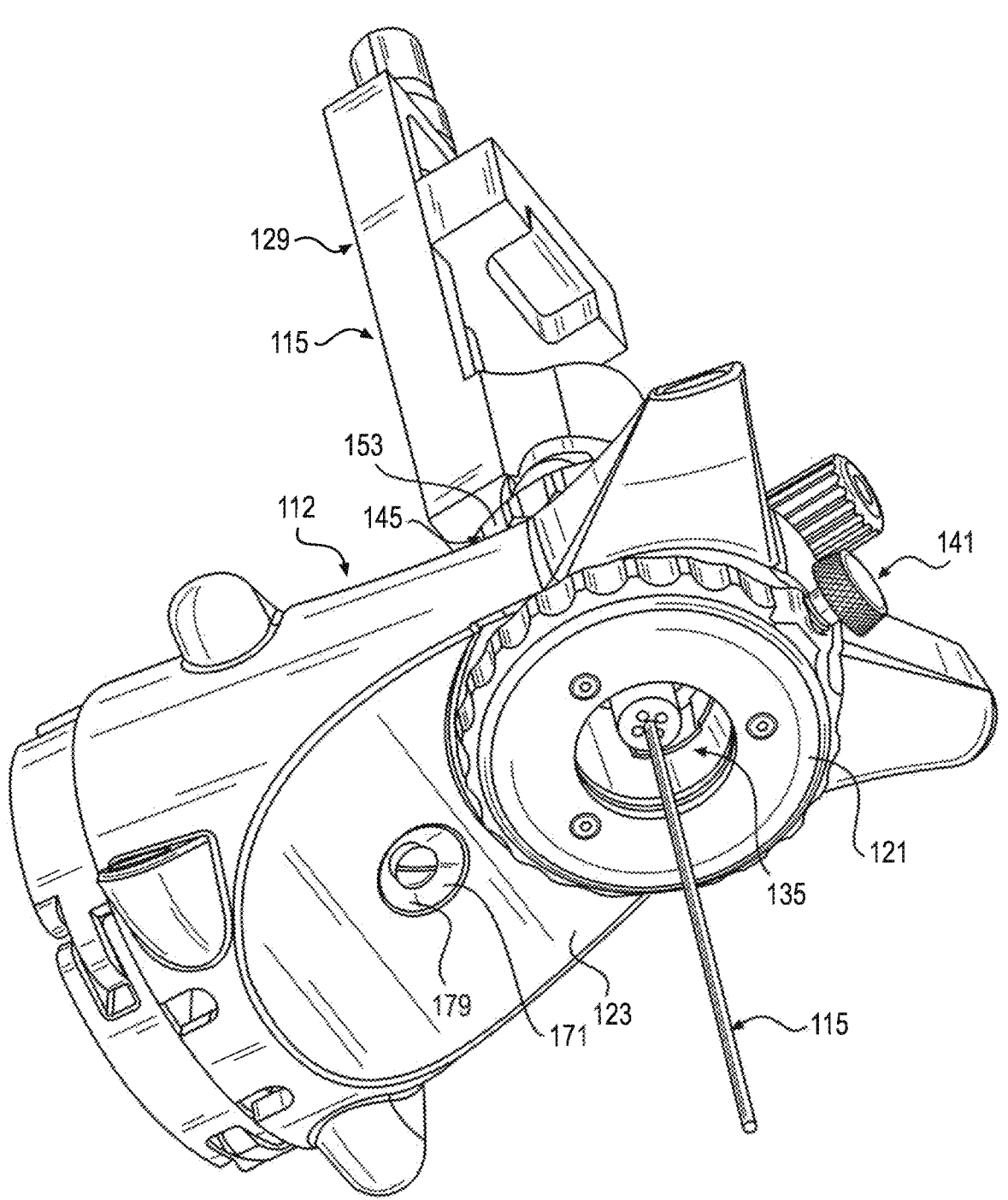
FIG. 15 is a bottom angle isometric view of yet another possible implementation of an end-effector according to the present disclosure.

Turning now to tool-insert locking mechanism 117 (FIG. 13, 17, 18), a connector 145 is configured to meet with and secure any one of the surgical tools 129 at their appropriate height, angle of orientation, and rotational position relative to the anatomical feature of the patient. In the illustrated implementation, connector 145 comprises a rotatable flange 147 which has at least one slot 149 formed therein to receive therethrough a corresponding tongue 151 associated with a selected one of the plurality of tools 129. So, for example, in FIG. 14, the particular electrode driver 115 has multiple tongues, one of which tongue 151 is shown. Rotatable flange 147, in some implementations, may comprise a collar 153, which collar, in turn, has multiple ones of slots 149 radially spaced on a proximally oriented surface 155, as best seen in FIG. 12. Multiple slots 147 arranged around collar 153 are sized or otherwise configured so as to receive therethrough corresponding ones of multiple tongues 151 associated with a selected one of the plurality of tools 129. Therefore, as seen in FIG. 13, multiple slots 149 and corresponding tongues 151 may be arranged to permit securing of a selected one of the plurality of tools 129 only when selected tool is in the correct, predetermined angle of orientation and rotational position relative to the anatomical feature of the patient. Similarly, with regard to the electrode driver shown in FIG. 14, tongues 151 (one of which is shown in a cutaway of FIG. 14) have been received in radially spaced slots 149 arrayed so that electrode driver 115 is received at the appropriate angle of orientation and rotational position.

Figure 17:
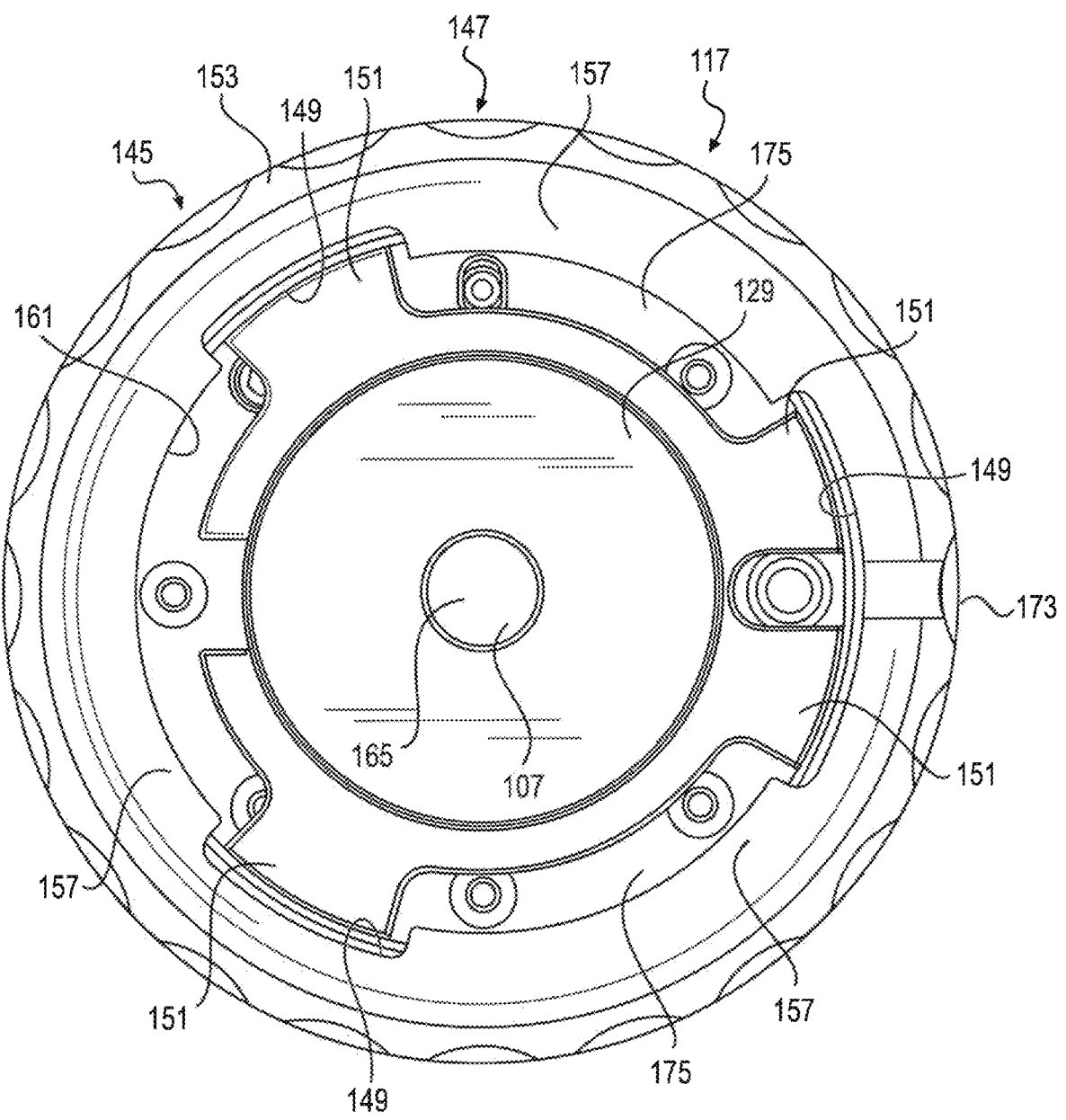
FIGS. 17 and 18 are top plan views of one possible implementation of a tool insert locking mechanism of an end-effector according to the present disclosure.
Figure 18:
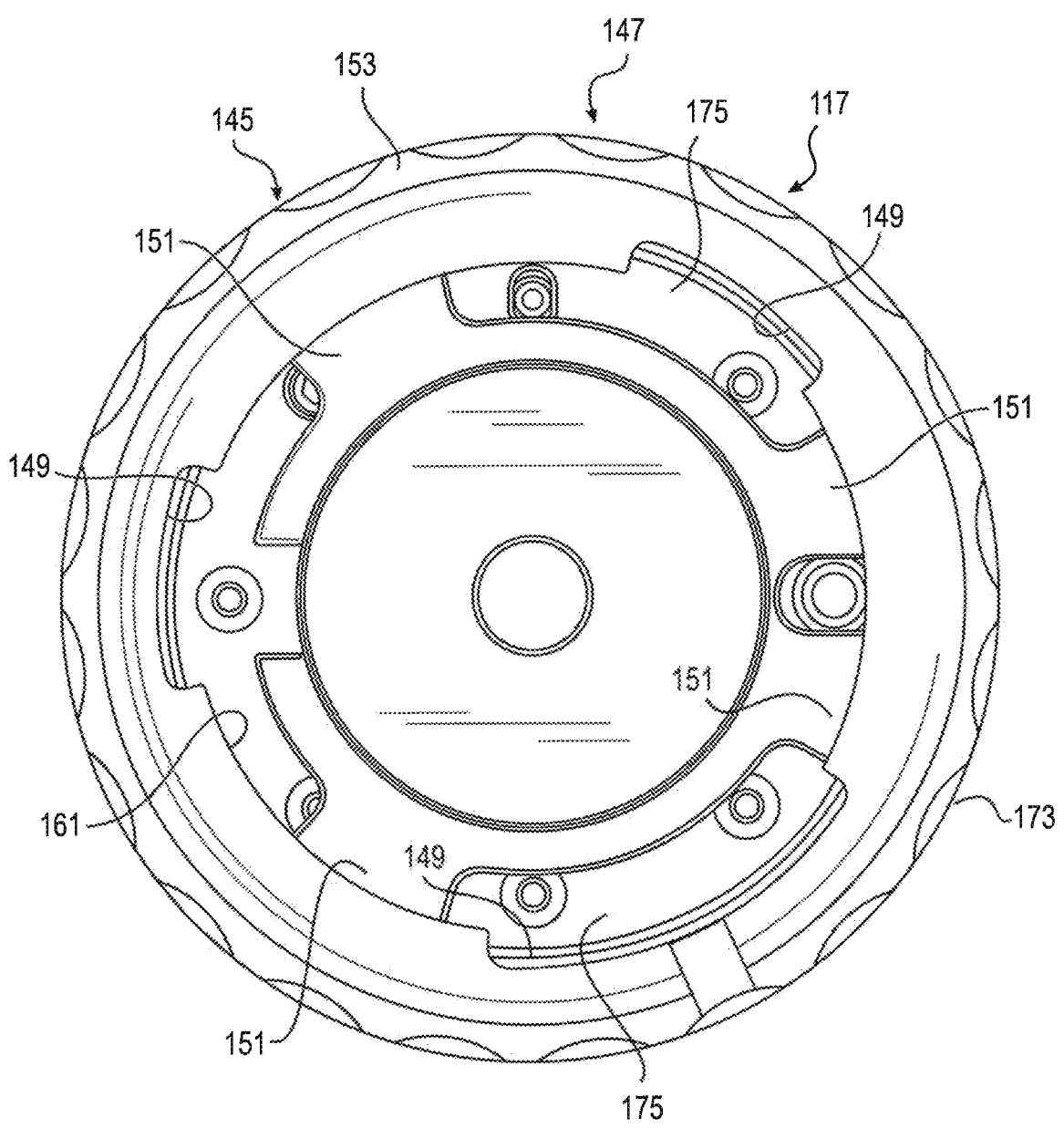

Rotatable flange 147 has, in this implementation, a grip 173 to facilitate manual rotation between an open and closed position as shown in FIGS. 17 and 18, respectively. As seen in FIG. 17, multiple sets of mating slots 149 and tongues 151 are arranged at different angular locations, in this case, locations which may be symmetric about a single diametric chord of a circle but otherwise radially asymmetric, and at least one of the slots has a different dimension or extends through a different arc length than other slots. In this slot-tongue arrangement, and any number of variations contemplated by this disclosure, there is only one rotational position of the tool 129 (or adapter 155 discussed later) to be received in tool-insert locking mechanism 117 when rotatable flange 147 is in the open position shown in FIG. 17. In other words, when the user of system 100 moves a selected tool 129 (or tool adapter 155) to a single appropriate rotational position, corresponding tongues 151 may be received through slots 149. Upon placement of tongues 151 into slots 149, tongues 151 confront a base surface 175 within connector 145 of rotatable flange 147. Upon receiving tongues 151 into slots 149 and having them rest on underlying base surface 175, dimensions of tongues 151 and slots 149, especially with regard to height relative to rotatable flange 147, are selected so that when rotatable flange 147 is rotated to the closed position, flange portions 157 are radially translated to overlie or engage portions of tongues 151, such engagement shown in FIG. 18 and affixing tool 129 (or adapter 155) received in connector 145 at the desired, predetermined height, angle of orientation, and rotational position relative to the anatomical feature of the patient.

Tongues 151 described as being associated with tools 129 may either be directly connected to such tools 129, and/or tongues 151 may be located on and mounted to the above-mentioned adapter 155, such as that shown in FIGS. 12, 17 and 18, such adapter 155 configured to interconnect at least one of the plurality of surgical tools 129 with end-effector 112. In the described implementation, adapter 155 includes two operative portions—a tool receiver 157 adapted to connect the selected one or more surgical tools 129, and the second operative part being one or more tongues 151 which may, in this implementation, be mounted and connected to the distal end of adapter 155.

Adapter 155 has an outer perimeter 159 which, in this implementation, is sized to oppose an inner perimeter 161 of rotatable flange 147. Adapter 155 extends between proximal and distal ends 163, 165, respectively and has an adapter bore 167 extending between ends 163, 165. Adapter bore 167 is sized to receive at least one of the plurality of surgical tools 129, and similarly, the distance between proximal and distal ends 163, 165 is selected so that at least one of tools 129 is secured to end-effector 112 at the predetermined, appropriate height for the surgical procedure associated with such tool received in adapter bore 167.

In one possible implementation, system 100 includes multiple ones of adapter 155, configured to be interchangeable inserts 169 having substantially the same, predetermined outer perimeters 159 to be received within inner perimeter 161 of rotatable flange 147. Still further in such implementation, the interchangeable inserts 169 have bores of different, respective diameters, which bores may be selected to receive corresponding ones of the tools 129 therein. Bores 167 may comprise cylindrical bushings having inner diameters common to multiple surgical tools 129. One possible set of diameters for bores 167 may be 12, 15, and 17 millimeters, suitable for multiple robotic surgery operations, such as those identified in this disclosure.

In the illustrated implementation, inner perimeter 161 of rotatable flange 147 and outer perimeter 159 of adapter 155 are circular, having central, aligned axes and corresponding radii. Slots 149 of rotatable flange 147 extend radially outwardly from the central axis of rotatable flange 147 in the illustrated implementation, whereas tongues 151 of adapter 155 extend radially outwardly from adapter 155.

In still other implementations, end-effector 112 may be equipped with at least one illumination element 171 (FIGS. 14 and 15) orientable toward the anatomical feature to be operated upon. Illumination element 171 may be in the form of a ring of LEDs 177 (FIG. 14) located within adapter 167, which adapter is in the form of a bushing secured to tool locking mechanism 117. Illumination element 171 may also be a single LED 179 mounted on the distal surface 123 of end-effector 112. Whether in the form of LED ring 177 or a single element LED 179 mounted on distal surface of end-effector 112, or any other variation, the spacing and location of illumination element or elements 171 may be selected so that tools 129 received through bore 133 of end-effector 112 do not cast shadows or otherwise interfere with illumination from element 171 of the anatomical feature being operated upon.

The operation and associated features of end-effector 112 are readily apparent from the foregoing description. Tool stop 121 is rotatable, selectively lockable, and movable between engaged and disengaged positions, and a sensor prevents movement of end-effector 112 when in such disengaged position, due to the potential presence of a tool which may not be advisably moved during such disengaged position. Tool-insert locking mechanism 117 is likewise rotatable between open and closed positions to receive one of a plurality of interchangeable inserts 169 and tongues 151 of such inserts, wherein selected tools 129 may be received in such inserts 169; alternately, tongues 151 may be otherwise associated with tools 129, such as by having tongues 151 directly connected to such tools 129, which tongue-equipped tools likewise may be received in corresponding slots 149 of tool-insert locking mechanism 117. Tool-insert locking mechanism 117 may be rotated from its open position in which tongues 151 have been received in slots 149, to secure associated adapters 155 and/or tools 129 so that they are at appropriate, respective heights, angles of orientation, and rotational positions relative to the anatomical feature of the patient.

For those implementations with multiple adapters 155, the dimensions of such adapters 155, including bore diameters, height, and other suitable dimensions, are selected so that a single or a minimized number of end-effectors 112 can be used for a multiplicity of surgical tools 129. Adapters 155, such as those in the form of interchangeable inserts 169 or cylindrical bushings, may facilitate connecting an expanded set of surgical tools 129 to the end-effector 112, and thus likewise facilitate a corresponding expanded set of associated surgical features using the same end-effector 112.

Another possible embodiment of surgical robot system 100 shown in FIG. 1A is described below and shown with reference to FIGS. 21-24.

A base in the form of a dynamic reference base ("DRB") 1040 is shown and described and is suitable for use with any suitable registration fixture or registration system operatively associated with surgical robot system 100, such as systems 500 (FIGS. 5A-5C), 600 (FIGS. 6A-6B), 700 (FIG. 7), 800 (FIGS. 8A-8B), and 900 (FIG. 9). DRB 1040 includes features and corresponding structures, as shown and described below, to enable DRB 1040 not only to be attached relative to the patient anatomy of surgical interest and to be used in associated registration processes either pre- or intra-operatively, but also to be detached and reattached without losing its previously determined registration. Such features have advantages such as increasing workflow flexibility by allowing surgeons and other medical practitioners to use robotic system 100 and its related registration systems more efficiently, potentially avoiding the need for re-registration, as may be needed when using robot system 100 in both the non-sterile and sterile stages of a procedure, or to otherwise increase efficiency by avoiding loss of registration when DRB 1040 is attached and registered at one point in time, detached, and then subsequently reattached.

DRB 1040 may be used and secured in manners similar to those discussed with reference to DRBs 540, 640, 740, 840, and 940, except that DRB 1040 includes features, as mentioned, to permit detachment and reattachment without loss of previously determined registration under most circumstances. DRB 1040 may comprise or be integral with any suitable registration fixture, or DRB 1040 may be connected to or otherwise may be associated with any of the various registration fixtures shown and described herein with reference to FIGS. 1-9. DRB 1040 likewise may be used in still further alternate embodiments associated with any of the wide variety of registration hardware and related methods, whether by computerized tomography (CT) or fluoroscopy (fluoro) registration techniques and likewise may utilize either frame-based configurations or frameless arrangements. In the implementations illustrated in FIGS. 5A-5C, 6A-6B, 7, 8A-8B, and 9, DRB 1040 may be detachably mounted to a mounting arm, auxiliary mounting arm, or other suitable location on the registration fixture, including, for example, a patient stabilization device, stereotactic frame, FRA fixtures, and the like, with mount 1051 suitably interposed between DRB 1040 and its fixation location on the registration fixture.

To the ends of enhancing registration of DRB 1040 during repeated attachments and detachments, DRB 1040 includes or is operatively associated with structures which permit DRB 1040 to be mounted not only detachably, but without losing registration in most circumstances. In the illustrated implementation, such structures include a mount 1051. Referring to FIGS. 21-24, in one suitable implementation, mount 1051 is secured to one planar surface 1053 of DRB 1040, which, in the orientation shown in FIGS. 21 and 22, may be thought of as the underside of DRB 1040. Opposite underside surface 1053, DRB 1040 has a planar surface 1057 which, in the orientation of FIG. 21, may be considered the upper or top side of DRB 1040 as shown. Mount 1051 is interposed between DRB 1040, on the one hand, and the registration fixture, mounting arm, or other component of robotic system 100, on the other hand. A suitable fastener, such as a manually operable threaded handle or screw 1055 secures both DRB 1040 and interposed mount 1051 to the appropriate location on the registration fixture or other location. In the illustrated implementation, screw 1055 is threadably received in opposing threaded portions of the registration fixture or other mounting location, so as to clamp or otherwise hold DRB 1040 to mount 1051. DRB 1040 has a set of tracking markers, such as those shown in FIGS. 5-9 as 542, 642, 742, 842, and 942, each such tracking marker secured at a respective one of posts 1059.

Certain features on opposing surfaces of DRB 1040 and mount 1051 act to position DRB 1040 consistently between successive attachments, detachments, and reattachments. Given the consistent reattachment position and orientation afforded by DRB 1040 and its associated mount 1051, a previously determined position of the set of tracking markers mounted to DRB 1040, would also be identical or substantially similar to a subsequently determined position of such tracking markers, if and when DRB 1040 is detached and then reattached. As such, the registration procedure associated with the determination of tracking marker positions relative to components of the robotic surgical system itself, such as the robot arm, patient fixation devices, registration fixtures, and the anatomical feature which is of interest, all such registration parameters may be replicated between successive attachments, detachments, and reattachments of DRB 1040 and its associated mount 1051, under most circumstances.

Figure 22:
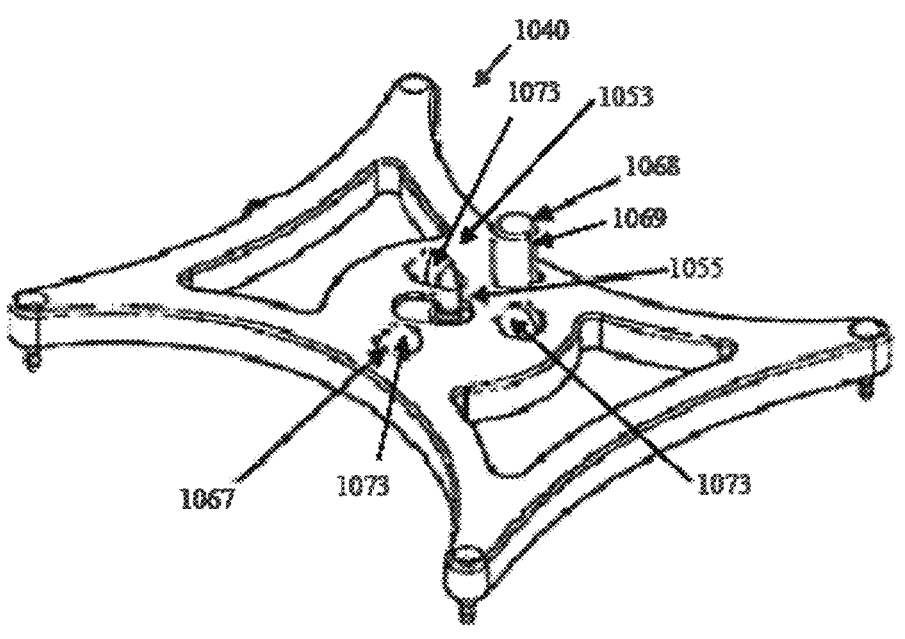
FIG. 22 is a second, isometric view of the detachable base of FIG. 21 turned over to show the underside of one of the surfaces.
Figure 23:
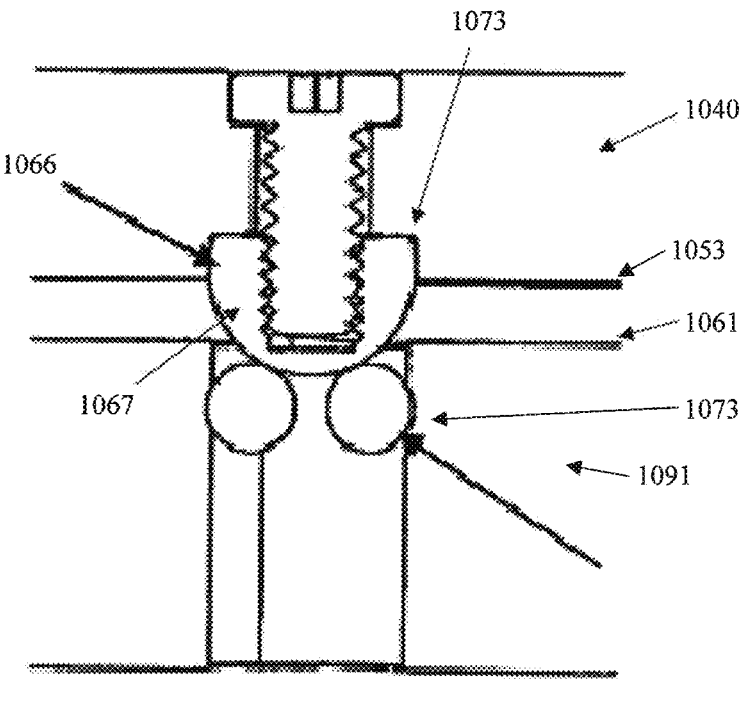
FIG. 23 is a side, cross-sectional, enlarged view of components of detachable components of a registration fixture according to various implementations of this disclosure.
Figure 24:
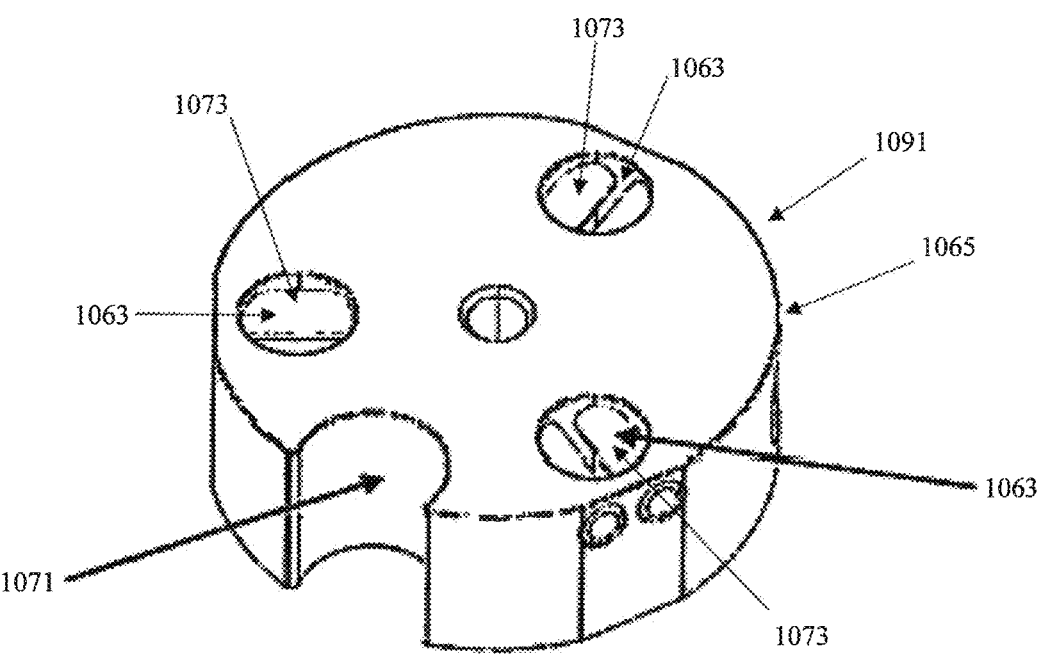
FIG. 24 is an isometric view of a suitable mount according to certain implementations of this disclosure.

Referring more particularly to FIGS. 22-24, mount 1051 has a planar mounting surface 1061 which is brought into an opposing relationship with surface 1053 of DRB 1040 when secured to the appropriate component of robot system 100. Mounting surface 1061 comprises a central area with portions extending therefrom to terminate in an arcuate perimeter 1065, which perimeter, in this implementation, comprises a circle. Mounting surface 1061 has disposed thereon three sets of receiving pins 1063 at radially spaced locations on mounting surface 1061. As such, receiving pins 1063, in this implementation, are spaced about such arcuate perimeter by angles ranging from 110° to 130°, or at about 120°.

Underside 1053 of DRB 1040 which, when suitably connected, opposes mounting surface 1061 of mount 1051, includes contacts 1066 at radially spaced locations corresponding to those of receiving pins 1063. Such contacts 1066 in this implementation may be in the form of hemispherical surfaces 1067 which are sized and otherwise configured to engage opposing portions on each of the two pins of respective pairs of receiving pins 1063 when DRB 1040 and mount 1051 are clamped to each other.

Detachable DRB 1040 and its corresponding mount 1051 are further configured so as to be positionable in a single orientation by means of the selective engagement of at least one keyed flange 1068. Keyed flange 1068 in this implementation comprises mating portions located on respective opposing surfaces of mount 1051 and detachable DRB 1040, such mating portions comprising a post 1069 extending from one of the opposing surfaces of the mount and the base and a corresponding cut-out 1071 formed in the other of the opposing surfaces. In this implementation, cut-out 1071 is formed in the body of mount 1051 and receives therein post 1069 extending from underside 1053 of detachable DRB 1040. Cut-out 1071 may be sized or otherwise adapted to receive post 1069 therein with little to no clearance, so as to further assure attachment of DRB 1040 and mount 1051 in the required single orientation and position.

Respective receiving pins 1063 and opposing contacts 1066 comprise a plurality of mounting members 1073 for detachably securing DRB 1040 and mount 1051, and along with keyed flange 1068, cause DRB 1040 and its associated tracking markers 1042 to be positionable in a consistent orientation between successive detachments and reattachments relative to other components against which tracking markers 1042 have been registered. Although mounting members 1073 comprise opposing sets of receiving pins 1063 and hemispherical surfaces 1067 in this implementation, mounting members 1073 may assume alternate forms, including one or more contacts on either one of the mount 1041 and the dynamic reference base 1040 and one or more receiving pins having a configuration or configurations different from the pairs of cylindrical receiving pins shown and described in FIGS. 21-24. Whatever the exact configuration of mounting members 1073, together they form a kinematic mount having opposing portions between the mount 1051 and DRB 1040 to urge such components to predetermined mating positions, such predetermined mating positions characterized by respective angular orientations that vary by less than 15% between successive detachments and reattachments of the mount 1041 and base 1040.

Robotic system 100 may include one or more processor circuits, memory accessible to such processor circuit or circuits, and suitable machine readable instructions to perform various registration functions or otherwise take advantage of the above-described detachable DRB 1040, mount 1041, and its kinematic mounting members 1073 permitting attachment and reattachment without significant variation in position or orientation. To that end, tracking markers associated with DRB 1040 may comprise four of the tracking markers as shown in previous embodiments herein at spaced locations defining corners of a quadrilateral and the corresponding tracking marker positions may likewise correspond to positions registered using the registration systems previously disclosed herein. The mounting locations of tracking markers may comprise registered verification values in such registration systems.

Suitable programming, when executed, may compare first and second sets of verification values corresponding to multiple attachments of DRB 1040 to registration fixtures disclosed hereunder. Thus, for example, suitable programming may compare the mounting locations of tracking markers on DRB 1040 pre-operatively, such as when the patient is being draped in a nonsterile field, and a subsequent set of verification values may correspond to intra-operative reattachment of DRB 1040. Programming determines substantial identity or non-identity of the two sets of verification values, and the kinematic mount and other features of mounting members 1073 discussed herein assure substantial identity between the two sets of verification values under most circumstances.

Robotic system 100 may include suitable programming in the form of a navigation system to perform navigational functions preoperatively and in a nonsterile environment, such navigation functions facilitating the marking of incisions and the performance of navigation integrity checks. In the context of such navigation functions, instructions may be executed preoperatively after determination of a first set of tracking marker positions, as well as a corresponding first position and first orientation of a registration fixture associated with a contemplated robotic surgical procedure. Thereafter, navigation functions may be executable by robotic system 100 intra-operatively, after detachment and reattachment of DRB 1040 to mount 1051, and after a determination of identity between the first set of tracking marker positions and a second set of the tracking marker positions.

Use and operation of the features and structures of a registration fixture equipped with DRB 1040 and mount 1051 is readily appreciated from the foregoing description. In one possible method, performance of a cranial procedure on a patient takes place with a computer-implemented surgical robot of a corresponding robot system. In the contemplated procedure, a sterile field is established and, prior to establishing such sterile field, the patient is registered, including marking, incision points for the cranial procedure, and various components of the robotic system are registered with respect to each other and/or anatomical features of the patient related to the contemplated operation. The step of registering the patient may include performing a first, detachable mounting of a plurality of tracking markers in a first predetermined position and corresponding first orientation relative to a patient registration fixture and determining, by means of computer instructions executed by a computer processor, a plurality of tracking marker positions corresponding to the aforesaid plurality of tracking markers. The procedure may then involve detaching the plurality of tracking markers, such as would occur upon detachment of DRB 1040 on which such plurality of tracking markers are secured in known positions.

Subsequently, after establishing a sterile field, DRB 1040 may be reattached or remounted, along with its plurality of tracking markers, by aligning the mating, mounting members 1073 on opposing surfaces of DRB 1040 and mount 1051. Such mounting members 1073 thus have the effect of realigning the tracking markers on DRB 1040 with the previously determined registration of the patient registration fixture to which DRB 1040 is being attached. As such, tracking markers and the registration fixture are only mountable relative to each other in a second, position which has the same registration as the first previously determined position.

In still other possible methods according to this disclosure, computer instructions of the robotic system may mark incisions or otherwise perform registration functions using GPS-assisted navigation instructions of the system. The system likewise may perform navigational integrity checks before or after establishing the sterile field, pre-operatively or intra-operatively, and detachable DRB 1040 and corresponding mount 1051 assure the success of such navigational integrity checks.

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Although several embodiments of inventive concepts have been disclosed in the foregoing specification, it is understood that many modifications and other embodiments of inventive concepts will come to mind to which inventive concepts pertain, having the benefit of teachings presented in the foregoing description and associated drawings. It is thus understood that inventive concepts are not limited to the specific embodiments disclosed hereinabove, and that many modifications and other embodiments are intended to be included within the scope of the appended claims. It is further envisioned that features from one embodiment may be combined or used with the features from a different embodiment(s) described herein. Moreover, although specific terms are employed herein, as well as in the claims which follow, they are used only in a generic and descriptive sense, and not for the purposes of limiting the described inventive concepts, nor the claims which follow. The entire disclosure of each patent and patent publication cited herein is incorporated by reference herein in its entirety, as if each such patent or publication were individually incorporated by reference herein. Various features and/or potential advantages of inventive concepts are set forth in the following claims.

The invention claimed is:

1. A method of performing a cranial procedure on a patient with a computer-implemented surgical robot of a corresponding robot system, the method comprising:

registering a patient in a non-sterile field by performing a first, detachable mounting of a plurality of tracking markers relative to a registration fixture and determining, by means of computer instructions executed by a computer processor, a first position and first orientation of the plurality of tracking markers;

marking incision points for the cranial procedure to be performed;

detaching the plurality of tracking markers;

establishing a sterile field; and performing a second detachable mounting of the plurality of tracking markers.

2. The method of claim 1, wherein one or more of registering a patient or marking incision points is carried out by a programmed computer executing computer instructions of the robotic system to mark incisions using GPS-assisted navigation instructions of the system.

3. The method of claim 2, comprising performing navigational integrity checks before establishing the sterile field.

4. The method of claim 1, wherein performing a second detachable mounting of the plurality of tracking markers comprises preventing the plurality of tracking markers from being mounted other than in the first position and the first orientation.

5. The method of claim 1, wherein performing a second detachable mounting comprises mounting the plurality of tracking markers in a second position, wherein a registration of the second position is the same as a registration of the first position.

6. The method of claim 1, wherein the plurality of tracking markers are located on a dynamic reference base.

7. The method of claim 6, wherein performing a second detachable mounting of the plurality of tracking markers comprises aligning mating, mounting members on opposing surfaces of the dynamic reference base and a mount.

8. The method of claim 7, wherein the mounting members realign the plurality of tracking markers on the dynamic reference base with a registration of the patient established in the non-sterile field.

* * * * *